US007871996B2

(12) United States Patent
Weinberg et al.

(10) Patent No.: US 7,871,996 B2
(45) Date of Patent: Jan. 18, 2011

(54) METHODS OF INHIBITING NITRIC OXIDE SYNTHASE USING CORRIN DERIVATIVES

(75) Inventors: Joe Brice Weinberg, Durham, NC (US); Dipak Kumar Ghosh, Durham, NC (US)

(73) Assignee: The United States of America as represented by the Department of Veterans Affairs, Washington, DC (US)

( * ) Notice: Subject to any disclaimer, the term of this patent is extended or adjusted under 35 U.S.C. 154(b) by 129 days.

(21) Appl. No.: 11/904,747

(22) Filed: Sep. 28, 2007

(65) Prior Publication Data

US 2008/0153798 A1 Jun. 26, 2008

Related U.S. Application Data

(60) Provisional application No. 60/849,258, filed on Oct. 4, 2006.

(51) Int. Cl.
*A61K 31/555* (2006.01)
*A61P 43/00* (2006.01)

(52) U.S. Cl. ..................................... 514/186
(58) Field of Classification Search ........................ None
See application file for complete search history.

(56) References Cited

U.S. PATENT DOCUMENTS

| | | | | |
|---|---|---|---|---|
| 5,449,688 | A | * | 9/1995 | Wahl et al. .................. 514/546 |
| 5,767,103 | A | * | 6/1998 | Greenberg et al. ............. 514/52 |
| 2008/0227746 | A1 | * | 9/2008 | Boss et al. .................... 514/52 |

OTHER PUBLICATIONS

Reddy: Resonance, Jun. 1999, p. 67-77.*
Weinberg et al. (Blood (ASH Annual Meeting Abstracts), 106: Abstract 2225, Dec. 2005).*
Merck Manual regarding Alzheimer's disease, (2007).*
Merck Manual regarding Infertility, (2008).*
Akaike, Akinori et al., "Protective Effects of a Vitamin $B_{12}$ Analog, Methylcobalamin, Against Glutamate Cytotoxicity in Cultured Cortical Neurons," *European Journal of Pharmacology*, 1993, 241:1-6—Exhibit 1.
Alderton, Wendy K. et al., "Nitric Oxide Synthases: Structure, Function and Inhibition," *Biochem J*, 2001, 357:593-615—Exhibit 2.
Babu, Boga Ramesh et al., "Design of Isoform-Selective Inhibitors of Nitric Oxide Synthase," *Current Opinion in Chemical Biology*, 1998, 2:491-500—Exhibit 3.
Broderick, Kate E. et al., "Nitric Oxide Scavenging by the Cobalamin Precursor Cobinamide," *The Journal of Biological Chemistry*, 2005, 280:8678-85—Exhibit 4.
Brouwer, Marius et al., "Nitric Oxide Interactions With Cobalamins: Biochemical and Functional Consequences," *Blood*, 1996, 88:1857-64—Exhibit 5.
Durante, William et al., "Arginase: A Critical Regulator of Nitric Oxide Synthesis and Vascular Function," *Clin Exp Pharmacol Physiol*, 2007, 34:906-11—Exhibit 6.

Frick, Kevin K. and David A. Bushinsky, "Metabolic Acidosis Stimulates RANKL RNA Expression in Bone Through a Cyclo-Oxygenase-Dependent Mechanism," *Journal of Bone and Mineral Research*, 2003, 18:1317-25—Exhibit 7.
Gao, Ying Tong et al., "Thermodynamics of Oxidation-Reduction Reactions in Mammalian Nitric-Oxide Synthase Isoforms," *The Journal of Biological Chemistry*, 2004, 279:18759-66—Exhibit 8.
Ghosh, Dipak K. et al., "Host Response to Infection: the Role of CpG DNA in Induction of Cyclooxygenase 2 and Nitric Oxide Synthase 2 in Murine Macrophages," *Infection and Immunity*, 2001, 69:7703-10—Exhibit 9.
Greenberg Stan S. et al., "Hydroxocobalamin (Vitamin B12a) Prevents and Reverses Endotoxin-Induced Hypotension and Mortality in Rodents: Role of Nitric Oxide," *The Journal of Pharmacology and Experimental Therapeutics*, 1995, 273:257-65—Exhibit 10.
Hibbs, John B., Jr. et al., "Macrophage Cytotoxicity: Role for L-Arginine Deiminase and Imino Nitrogen Oxidation to Nitrite," *Science*, 1987, 235:473-6—Exhibit 11.
Hibbs, John B., Jr. et al., "Nitric Oxide: A Cytotoxic Activated Macrophage Effector Molecule," *Biochemical and Biophysical Research Communications*, 1988, 157:87-94 and Erratum 157:624—Exhibit 12.
Houeto, Paul et al., "Pharmacokinetics of Hydroxocobalamin in Smoke Inhalation Victims," *Clinical Toxicology*, 1996, 34:397-404—Exhibit 13.
Jenkinson, Karl M. et al., "Hydroxocobalamin and Haemoglobin Differentiate Between Exogenous and Neuronal Nitric Oxide in the Rat Gastric Fundus," *European Journal of Pharmacology*, 1995, 275:145-52—Exhibit 14.
Józkowicz, Alicja and Józef Dulak, "Effects of Protoporphyrins on Production of Nitric Oxide and Expression of Vascular Endothelial Growth Factor in Vascular Smooth Muscle Cells and Macrophages," *Acta Biochimica Polonica*, 2003, 50:69-79—Exhbit 15.
Kikuchi, Masashi et al., "Protective Effects of Methylcobalamin, a Vitamin $B_{12}$ Analog, Against Glutamate-Induced Neurotoxicity in Retinal Cell Culture," *Invest Ophtahlmol Vis Sci.*, 1997, 38:848-54—Exhibit 16.
Kruszyna, Harriet et al., "Spectroscopic Studies of Nitric Oxide (NO) Interactions with Cobalamins: Reaction of NO with Superoxocobalamin(III) Likely Accounts for Cobalamin Reversal of the Biological Effects of NO," *The Journal of Pharmacology and Experimental Therapeutics*, 1998, 285:665-71—Exhibit 17.
Li, C.G. and M. J. Rand, "Effects of Hydroxocobalamin and Haemoglobin on NO-Mediated Relaxations in the Rat Anococcygeus Muscle," *Clinical and Experimental Pharmacology and Physiology*, 1993, 20:633-40—Exhibit 18.
Li, Jianrong et al., "Nitric Oxide Reversibly Inhibits Seven Members of the Caspase Family Via S-Nitrosylation," *Biochemical and Biophysical Research Communication*, 1997, 240:419-24—Exhibit 19.
Li, Muyao et al., "The Weight Loss Elicited by Cobalt Protoporphyrin is Related to Decreased Activity of Nitric Oxide Synthase in the Hypothalamus," *J. Appl. Physiol.*, 2006, 1983-91—Exhibit 20.

(Continued)

*Primary Examiner*—Ardin Marschel
*Assistant Examiner*—Bong-Sook Baek
(74) *Attorney, Agent, or Firm*—Mandel & Adriano

(57) ABSTRACT

The present invention provides methods of inhibiting nitric oxide synthase (NOS) using corrin derivatives that bind NOS but do not bind NO. It also provides methods of inhibiting NOS in vivo by administering corrin derivatives, and methods of treating diseases and medical conditions using this inhibition of NOS.

3 Claims, 9 Drawing Sheets

OTHER PUBLICATIONS

Lim, Mark D. et al., "NO and $NO_x$ Interactions with Group 8 Metalloporphyrins," *Journal of Inorganic Biochemistry*, 2005, 99:151-65—Exhibit 21.

Mannick, Joan B. et al., "Fas-Induced Caspase Denitrosylation," *Science*, 1999, 284:651-54—Exhibit 22.

Moncada, Salvador and Anne Higgs, "The L-Arginine-Nitric Oxide Pathway," *The New England Journal of Medicine*, 1993, 329:2002-12—Exhibit 23.

Morris, Sidney M., Jr., "Arginine Metabolism: Enzymology, Nutrition and Clinical Significance, Enzymes of Arginine Metabolism," *The Journal of Nutrition*, 2004, 134:2743S-7S—Exhibit 24.

Newman, Elena et al., "Differential Activation of Nitric-oxide Synthase Isozymes by Calmodulin-Troponin C Chimeras," *The Journal of Biological Chemistry*, 2004, 279:33547-57—Exhibit 25.

Rochelle, Lori G. et al., "Interactions Between Hydroxocobalamin and Nitric Oxide (NO): Evidence for a Redox Reaction Between NO and Reduced Cobalamin and Reversible NO Binding to Oxidized Cobalamin," *The Journal of Pharmacology and Experimental Therapeutics*, 1995, 275:48-52—Exhibit 26.

Sharara, Ala I. et al., "Interferon (IFN) α Activation of Human Blood Mononuclear Cells In Vitro and In Vivo for Nitric Oxide Synthase (NOS Type 2 mRNA and Protein Expression: Possible Relationship of Induced NOS2 to the Anti-Hepatitis C Effects of IFN α In Vivo," *The Journal of Experimental Medicine*, 1997, 186:1495-1502—Exhibit 27.

Sharma, Vijay S. et al., "Reactions of Nitric Oxide with Vitamin $B_{12}$ and Its Precursor, Cobinamide," *Biochemistry*, 2003, 42:8900-8—Exhibit 28.

Stabler, Sally P. et al., "Inhibition of Cobalamin-dependent Enzymes by Cobalamin Analogues in Rats," *J. Clin. Invest.*, 1991, 87:1422-30—Exhibit 29.

Stamler, Jonathan S. et al., "Biochemistry of Nitric Oxide and its Redox-Activated Forms," *Science*, 1992, 258:1898-1902—Exhibit 30.

Stuehr, Dennis J., "Arginine Metabolism: Enzymology, Nutrition and Clinical Significance, Enzymes of the L-Arginine to Nitric Oxide Pathway," *The Journal of Nutrition*, 2004, 134:2748S-51S—Exhibit 31.

Stuehr, Dennis J., "Mammalian Nitric Oxide Synthases," *Biochimica et Biophysica Acta*, 1999, 1411:217-30—Exhibit 32.

van der Kuy, P-HM et al., "Hydroxocobalamin, a Nitric Oxide Scavenger, in the Prophylaxis of Migraine: An Open, Pilot Study," *Cephalalgia*, 2002, 22:513-9—Exhibit 33.

Weinberg, J.B. et al., "Human Mononuclear Phagocyte Inducible Nitric Oxide Synthase (iNOS): Analysis of iNOS mRNA, iNOS Protein, Biopterin and Nitric Oxide Production by Blood Monocytes and Peritoneal Macrophages," *Blood*, 1995, 86:1184-95—Exhibit 34.

Weinberg, J. Brice, "Nitric Oxide Production and Nitric Oxide Synthase Type 2 Expression by Human Mononuclear Phagocytes: A Review," *Molecular Medicine*, 1998, 4:557-91—Exhibit 35.

Wolff, Donald J. et al., "Inhibition of Nitric Oxide Synthase Isoforms by Porphyrins," *Archives of Biochemistry and Biophysics*, 1996, 333:27-34—Exhibit 36.

Forsyth, John C. et al., "Hydroxocobalamin as a Cyanide Antidote: Safety, Efficacy and Pharmacokinetics in Heavily Smoking Normal Volunteers," *Clinical Toxicology*, 1993, 31:277-94—Exhibit 37.

\* cited by examiner

3A

3B

3C

3D

A

B

METHODS OF INHIBITING NITRIC OXIDE SYNTHASE USING CORRIN DERIVATIVES

This application claims the priority of U.S. Ser. No. 60/849,258, the entirety of which is hereby incorporated by reference into this application.

The invention was also made in part with funding under Grant Number CA90548 awarded by the National Institutes of Health. The United States Government has certain rights in the invention.

Throughout this application various publications are referenced. The disclosures of these publications in their entirety are hereby incorporated by reference into this application in order to more fully describe the state of the art to which this invention pertains. The invention has been described with reference to various specific and preferred embodiments and techniques. However, it should be understood that many variations and modifications can be made while remaining within the spirit and scope of the invention.

TECHNICAL FIELD

This application generally relates to methods for inhibiting nitric oxide synthase (NOS) using corrin derivatives e.g., corrin derivatives that bind NOS but does not bind nitric oxide (NO). These methods can be used to treat diseases or medical conditions associated with elevated nitric oxide synthase levels. In one embodiment, the corrin derivative is a cobinamide such as dicyanocobinamide.

BACKGROUND OF THE INVENTION

Nitric oxide (NO) synthase (NOS) convert L-arginine to L-citrulline and NO in humans (1,2). NOS1 ("neural" NOS) and NOS3 ("endothelial" NOS) generally produce low levels of NO and are constitutively active, while inducible NOS (NOS2) is induced by cytokines and microbial factors. NO plays very important roles in normal physiology and in various pathologic processes (3-5). NO serves as a signal transducing molecule, an effector molecule for the stasis and killing of microbes (e.g., certain viruses, fungi, bacteria, and protozoa), and tumor cells. NO can also block apoptosis by S-nitrosylating caspases (6), and in resting, normal B lymphocytes, the active site cysteine of caspase 3 is nitrosylated (and inhibited by this nitrosylation), and it undergoes denitrosylation upon fas activation and apoptosis (7). NO controls smooth muscle contraction and thus influences vessel, bowel, bronchial, uterine, ureteral, and ductal contraction and tension (3).

There are three major isoforms of NOS (NOS1, NOS2, and NOS3) encoded by three separate genes (1). While these isoforms are noted in various cell types and tissues, NOS1 is found mainly in neural and muscle tissues; NOS2 in monocytes/macrophages, hepatocytes, and chondrocytes; and NOS3 in endothelial cells. A variety of agents have been demonstrated to inhibit the enzymatic function of NOS (1,8).

Most NOS inhibitors bind to the oxygenase domain of NOS with the guanidinium group of the inhibitor binding to NOS glutamate (8). Investigators described the importance of arginine in macrophage-mediated cytotoxicity, and demonstrated that arginine analogues such as $N^G$-mono-methylarginine (NMMA) could inhibit cytotoxicity (a function they later described as being related to NO production) (9,10). Since then, a variety of NOS inhibitors have been described (8).

Arginine analogues that act as classic competitive inhibitors (e.g., L-thiocitrulline) interact with the NOS oxygenase domain active site through hydrogen bonding interactions with glutamate by way of the guanidinium structural motif (8). These are generally isoform nonselective. "Slow on-slow off" arginine analogues (e.g., the S-alkyl-L-thiocitrullines) are not altered by NOS and also offer little isoform selectivity.

Mechanism-based inhibitors [suicide inhibitors (e.g., NIO)] offer the most isoform selectivity. Vinyl-L-NIO {$N^5$-(1-imino-3-butenyl)-L-ornithine} is an amidine analogue of this class that is markedly selective for NOS1. Likewise, L-NIL is very specific for NOS2.

NOS oxidase inhibitors (e.g., diphenyleneiodonium which also inhibits NADPH oxidase) inhibits NO formation, and inhibitors of NOS dimer formation (e.g., various pyrimidine-imidazoles) blocks NO formation by NOS.

NOS2-specific inhibitors have been targeted for use in a variety of conditions, most prominently septic shock and arthritis. NOS1-specific inhibitors have been targeted for use in psychiatric diseases such as depression and anxiety, and for neurodegenerative diseases such as Alzheimer's disease and amyotrophic sclerosis.

Others have taken a similar but different approach to negate the effects of NO. They have used compounds that bind, quench or scavenge NO to diminish NO effects (11). These scavengers include heme-containing compounds and cobalt-containing cobalamins and associated molecules. Certain cobalamins bind NO and thus quench their effects (12-23).

There exists a need to inhibit NOS, for example to treat migraine headaches and ill effects of inflammation. Heretofore, no one has ever reported that such cobalamins, or other corrin derivatives, can inhibit the activity of the NOS enzyme itself.

SUMMARY OF THE INVENTION

The present invention provides methods of inhibiting nitric oxide synthase (NOS) using corrin derivatives e.g., corrin derivatives that bind to and inhibit NOS but do not bind and quench/scavenge NO. It also provides methods of inhibiting NOS in vivo by administering corrin derivatives, and methods of treating diseases and medical conditions using this inhibition of NOS. Exemplary embodiments of the present invention are set forth as follows.

In an exemplary embodiment, the present invention provides a method of inhibiting nitric oxide synthase comprising contacting the nitric oxide synthase with a corrin derivative and thereby inhibiting nitric oxide production. In other particular embodiments, the corrin derivative inhibits nitric oxide synthase without sequestering, or while only weakly sequestering, nitric oxide.

In another exemplary embodiment, the present invention provides a method of inhibiting NOS in vivo, comprising administering a corrin derivative to the subject, thereby inhibiting NOS.

In an exemplary embodiment, the present invention provides a method for treating a subject having an inflammatory or neurological disease or medical condition associated with elevated nitric oxide synthase activity and/or NO overproduction comprising administering a corrin derivative so as to inhibit nitric oxide synthase and thereby treating the subject having the disease or medical condition. Examples of such diseases or medical conditions include, but are not limited to: infertility (e.g., gamete-sperm or ovum-defect), inflammation, conjunctivitis, cystitis, inflammatory bowel disease, nephritis, glomerulonephritis, hepatitis, arteritis, vasculitis, cerebritis, vaginitis, dermatitis, sinutisis, proctitis, otitis, pneumonitis, hypotension, arthritis, colitis, nephritis, meningitis, sepsis, septic or cardiogenic shock, myocardial infarction, asthma, or any other inflammatory disease, schizophrenia, migraine headache, psychosis, depression, anxiety, psoriasis, amylotropic sclerosis, Alzheimer's disease and other neurological conditions, pain, HIV/AIDS (including HIV encephalopathy), and leukemia (e.g., chronic lymphocytic leukemia) and other neoplastic conditions.

In an exemplary embodiment, the corrin derivative is a cobinamide. In a preferred embodiment, the cobinamide is dicyanocobinamide.

BRIEF DESCRIPTION OF THE FIGURES

FIG. 6 demonstrates inhibition of NO formation in cells.

BRIEF DESCRIPTION OF THE TABLE

Table 1 summarizes the inhibition of nitric oxide synthases by cobalamins and cobinamides. The effect of the indicated agents on the enzymatic activity of nNOS (NOS1), iNOS (NOS2) and eNOS (NOS3) were determined. Methylcobalamin and adenosylcobalamin were tested either having been exposed to light or not exposed to light. Results are displayed as the ED50 (uM).

DETAILED DESCRIPTION OF THE INVENTION

Definitions

Figure 1:
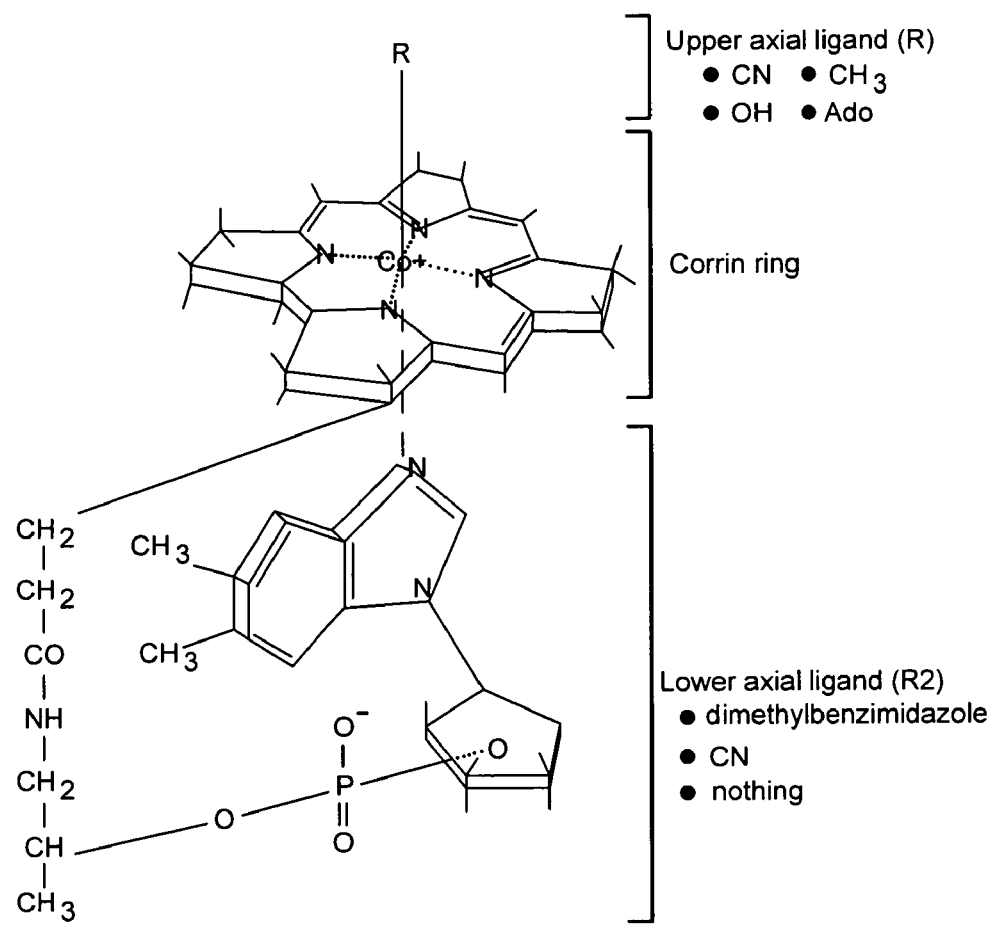
FIG. 1 shows the general structure of corrins/cobalamins. The figure demonstrates various upper axial ligands, the corrin ring, and a lower axial ligand. Hydroxocobalamin has a hydroxyl group at the R position. Cyanocobalamin has a cyano group at the R position. Methycobalamin and adenosylcobalamin have a methyl and adenosyl group, respectively, at the R position. Cobinamide lacks the lower axial ligand (R2) and has a hydroxyl group at the R position. Dicyanocobinamide has a cyano group as the lower axial ligand (R2) and at the R position. Abbreviations: CN, cyano; OH, hydroxo; $CH_3$, methyl; Ado, adenosyl.

A "corrin derivative" is defined as a molecule containing a central corrin ring that has attached to it an upper axial ligand and/or a lower axial ligand, as illustrated in FIG. 1. Many different chemical groups can serve as upper or lower axial ligands.

A "cobalamin" is a corrin derivative, as defined above, in which the lower axial ligand is dimethylbenzimidazole, and in which the upper axial ligand can be one of a variety of chemical groups (R), as illustrated in FIG. 1.

"Cobinamides" are a class of molecules that are corrin derivatives, as defined above, and that contain an R group as the upper axial ligand and no lower axial dimethylbenzimidazole. The lower axial ligand contains a different simple group (R2) as illustrated in FIG. 1.

"Dicyanocobinamide" is defined as, and is the specific name for, a specific molecule in the class of cobinamides in which both the upper and lower axial ligands are cyano groups.

"Nitric oxide synthase (NOS)" is the endogenous enzyme that converts L-arginine to L-citrulline plus nitric oxide (NO). Under conditions of low levels of the substrate L-arginine or the NOS co-factor tetrahydrobiopterin in a cell, nitric oxide synthase can be diverted from producing NO to produce superoxide.

For the purposes of this invention, the terms "quenching of nitric oxide (NO)", "scavenging of nitric oxide", "binding nitric oxide", "inhibiting nitric oxide" and "sequestering of nitric oxide" are synonymous, and may be used interchangeably. They are defined as decreasing, removing, or inactivating the biological activity of nitric oxide (NO).

For the purposes of this invention, "nitric oxide synthase (NOS) activity" is defined as the enzymatic activity of nitric oxide synthase in which L-arginine is converted to L-citrulline plus nitric oxide (NO) or in which oxygen is converted to superoxide.

For the purposes of this invention, the term "to contact nitric oxide synthase" with an inhibitor means to bind nitric oxide synthase with the inhibitor and decrease nitric oxide synthase activity.

For the purpose of this invention, "inhibition of nitric oxide synthase (NOS)" refers to any process in which the presence of a particular (inhibitory) agent reduces NOS activity. For example, the binding of a particular molecule to the active site of NOS may interfere with the normal catalytic activity of NOS, thus inhibiting NOS and reducing NOS activity.

For the purposes of this invention, "percent inhibition of nitric oxide synthase (NOS)" is defined as the amount (percentage) of decrease in NOS activity in the presence of a potential inhibitory agent of the NOS enzyme ("NOS activity experimental") compared to the amount of NOS activity when no potential inhibitory agent is present ("NOS activity control"). This decrease is expressed as a percentage using the formula: {[NOS activity control−NOS activity experimental/NOS activity control]×100}.

For the purposes of this invention, the term "blocking" and "inhibiting" is interchangeable and refers to a process in which an inhibitor (i.e. an inhibitory molecule or inhibitory agent) binds to or associates with a first molecule and sterically prevents a second molecule from binding to a site on the first molecule to which it would normally bind. An example of this is the binding or association of an inhibitory molecule to the active site of an enzyme so as to sterically block the normal binding of a substrate molecule to the active site.

For the purpose of this invention, "activation of methycobalamin or adenosylcobalamin by light" refers to the process by which methycobalamin and adenosylcobalamin are converted to hydroxocobalamin upon exposure to light. The resulting hydroxocobalamin, unlike methycobalamin or adenosylcobalamin, will strongly inhibit NOS, as noted elsewhere in this invention.

For the purposes of this invention, the term "agent" and "compound" means a molecule of interest that can be tested to determine its NOS binding and/or inhibitory ability. The term "agent" and "compound" are synonymous, and can be used interchangeably.

METHODS OF THE INVENTION

The present invention provides methods for inhibiting the enzyme, nitric oxide synthase (NOS). The method comprises contacting the NOS enzyme with a corrin derivative, thereby inhibiting NOS. When NOS is inhibited, its catalysis of nitric oxide (NO) production can be inhibited. Some corrin derivatives can also bind and sequester NO directly. In one embodiment, the present invention is directed to the ability of some corrin derivatives to bind and inhibit NOS directly, regardless of whether or not they also sequester NO directly.

In another embodiment of the invention, NOS is inhibited within a living organism by contacting NOS within that organism with a corrin derivative, thereby inhibiting NOS. In a further embodiment, NOS is inhibited within this living organism by administration of a corrin derivative to said organism.

In another embodiment of the invention, the method of the invention comprising contacting NOS with a corrin derivative, thereby inhibiting NOS, is used to treat a subject having an inflammatory or neurological disease or medical condition associated with nitric oxide synthase (NOS).

In another embodiment of the invention, a corrin derivative is administered to a subject having a disease or medical condition associated with increased NOS levels so that inhibiting NOS thereby treats the subject having the disease or medical condition associated with elevated NOS levels.

In one embodiment, the corrin derivative used in the methods of the invention is a cobalamin or cobinamide. In a preferred embodiment, the cobinamide is dicyanocobinamide.

In another embodiment of the invention, the inhibition of NOS by a corrin derivative inhibits NOS in a subject, or in a living organism, and may alter physiological processes or other processes affected by NOS.

In another embodiment of the invention, the inhibition of NOS by a corrin derivative can lower NO levels in the body of a subject, thereby treating any disease or medical condition that is regulated, at least in part, by NO.

When NOS is inhibited in a living organism or a subject through the administration of a corrin derivative, or by the contact of NOS with a corrin derivative, this inhibition of NOS can reduce intracellular production of nitric oxide (NO), secretion of NO by cells, or local or circulating NO levels in the subject or living organism. In a further embodiment, these cells may be macrophages, or they may be other cell types.

In another embodiment of the invention, the inhibition of NOS by a corrin derivative can lower superoxide levels in the body of a subject, thereby treating any disease or medical condition that is associated with superoxide or peroxynitrite. Limiting L-arginine can contribute to impairment in the host immune system inducing hypertension, aging, ischemia-reperfusion and diabetes (37, 38, 39).

When L-arginine is available, NOS converts L-arginine into L-citrulline and NO. However, when L-arginine is reduced the NOS enzymatic pathway shifts from producing NO to produce superoxide. Superoxide can react with NO to generate peroxynitrite, a molecule that can mediate inflammation and cell and tissue destruction.

Arginine availability can be reduced by many factors including, but not limited to, one or more of: reduced L-arginine production (e.g., genetic disorders), reduced L-arginine entry into cells by abnormal L-arginine transporters, increases L-arginine destruction by arginase (e.g., in severe infection, inflammation, and hemolysis), and with decreased L-arginine intake (e.g., markedly reduced L-arginine entry into the body or severe malnutrition).

In another embodiment of the invention, when a corrin derivative is used or administered so as to inhibit NOS, the corrin derivative inhibits NOS by blocking oxygen binding to heme, a step required for the NOS catalytic cycle.

In another embodiment of the invention, when a corrin derivative is administered to a subject, the subject may be a human or an animal.

In another embodiment of the invention, when a corrin derivative is administered to a subject, or to a living organism, the route of administration of this corrin derivative may be enteral (including, but not limited to, oral administration), or parenteral (including, but not limited to, intravenous, intramuscular, intraperitoneal, or intrapleural administration, or by inhalation), local or systemic or any other method of administration. Additional methods of administration include but are not limited to an implantable pump, continuous infusion, liposomes, vaginal or rectal suppositories, topical contact (e.g., topical creams or ointments), eye drops, vesicles, capsules, biodegradable polymers, hydrogels, controlled release patch and other injection methods (e.g., subcutaneous). Corrin derivatives are generally very hydrophilic and very soluble allowing for easy administration.

In another embodiment of this invention, when a corrin derivative is used or administered so as to inhibit NOS, the corrin derivative binds to and inhibits NOS without sequestering NO. In a further embodiment, the corrin derivative is a cobalamin or cobinamide. In a preferred embodiment, the cobinamide is dicyanocobinamide.

In another embodiment of this invention, when a corrin derivative is used or administered so as to inhibit NOS, the corrin derivative binds to and inhibits NOS and, in some embodiments, also sequestering NO. In a further embodiment, the corrin derivative is a cobalamin. In a preferred embodiment, the cobalamin is hydroxocobalamin.

In another embodiment of the invention, when a corrin derivative is used or administered, the corrin derivative may come from, but is not limited to, the cobinamide and cobalamin subgroups. Molecules in the cobinamide subgroup include, but are not limited to, cobinamide (Cbi), and dicyanocobinamide (CN2-Cbi). Molecules in the cobalamin subgroup include, but are not limited to, hydroxocobalamin (OH-Cbl), cyanocobalamin, methylcobalamin, and adenosylcobalamin. In a further embodiment of the invention, methylcobalamin or adenosylcobalamin may be activated by exposure to light. This exposure to light results in the cleavage of the methyl or adenosyl groups of these molecules, resulting in the production of the active molecule, hydroxocobalamin (OH-Cbl).

In a further embodiment of the invention, when methylcobalamin or adenososylcobalamin are administered to a subject or to a living organism, the subject or living organism is exposed to light at particular locations on the subject or living organism, resulting in the conversion of methylcobalamin or adenosylcobalamin to hydroxocobalamin at these particular locations, which then may result in NOS inhibition at these particular locations. In a further embodiment, this localized inhibition of NOS can result in lowered NO levels at these particular locations. In another embodiment, local inhibition of NOS alters physiological or other processes at these particular locations. In another embodiment, locally inhibited NOS treats a disease or medical condition at these particular locations. Examples of accessible area for selective illumination and "activation" of methylcobalamin or adenosylcobalamin to hydroxocobalamin include the skin, mucosa (e.g., mouth, bladder, vagina, uterus, oviducts, peritoneum, nasopharynx, bronchial tree, ears, and intravascular tree).

In a further embodiment, the invention provides a method for treating a disease or medical condition associated with NOS at a particular location or disease site in a subject comprising administering a light activated NOS inhibitor (e.g., methylcobalamin or adenosylcobalamin) to the disease site, exposing the NOS inhibitor to light so as to activate the inhibitor, thereby inhibiting NOS enzymatic activity. For example, Me-Cbl or Ado-Cbl could be administered intravenously and then accessible areas could be illuminated to selectively release the NOS inhibitor/NO quencher in a local area. Inhibition of NOS activity alters physiological or other processes at these particular locations or disease sites thereby treating the disease or medical condition associated with NOS in a subject.

NOS has multiple isoforms (NOS1, NOS2 and NOS3, for example). In a further embodiment of the invention, when NOS is inhibited, this inhibition is an inhibition of any of NOS1 and/or NOS2 and/or NOS3 and/or any other isoform of NOS. In a further embodiment, inhibition of NOS involves inhibition of more than one of the commonly known isoforms of NOS (e.g., NOS1, NOS2, and NOS3), simultaneously. In a further embodiment, the contacting of these NOS isoforms with a corrin derivative equally inhibits all isoforms present. In another embodiment, some NOS isoforms can be inhibited more than others. For example, if both NOS1 and NOS2 are present both isoforms can be inhibited equally or NOS2 can be inhibited more than NOS1. Alternatively, NOS1 can be inhibited more than NOS2. If both NOS1 and NOS3 are present both isoforms can be inhibited equally or NOS1 can be inhibited more than NOS3. Alternatively, NOS3 can be inhibited more than NOS1. If both NOS2 and NOS3 are present both isoforms can be inhibited equally or NOS2 can be inhibited more than NOS3. Alternatively, NOS3 can be inhibited more than NOS2. If NOS1, NOS2, and NOS3 are all present, they can all be inhibited equally. Alternatively, some isoforms can be inhibited more than others, in the following orders: NOS1>NOS2>NOS3; NOS1>NOS2=NOS3; NOS2>NOS1>NOS3; NOS2>NOS1=NOS3; NOS3>NOS1>NOS2; NOS3>NOS1=NOS2; NOS1>NOS3>NOS2; NOS2>NOS3>NOS1; NOS3>NOS2>NOS1.

In a further embodiment of the invention, when a corrin derivative is used to treat an inflammatory and/or neurological disease or medical condition or a disease or medical condition associated with elevated NOS levels (any of NOS1, NOS2 or NOS3 or combination thereof), this disease or medical condition can be a member of, but is not limited to, a group consisting of infertility (e.g., gamete-sperm or ovum-defect), inflammation, conjunctivitis, cystitis, inflammatory bowel disease, nephritis, glomerulonephritis, hepatitis, arteritis, vasculitis, cerebritis, vaginitis, dermatitis, sinutisis, proctitis, otitis, pneumonitis, hypotension, arthritis, colitis, nephritis, meningitis, sepsis, septic or cardiogenic shock, myocardial infarction, asthma, or any other inflammatory disease, schizophrenia, migraine headache, psychosis, depression, anxiety, psoriasis, amylotropic sclerosis, Alzheimer's disease and other neurological conditions, pain, HIV/AIDS (including HIV encephalopathy), and leukemia (e.g., chronic lymphocytic leukemia) and other neoplastic conditions.

In an embodiment of the invention, the corrin derivative can be administered to a subject in a dosage relative to the weight of the subject or in a dosage not related to the weight of the subject. It would be clear to one skilled in the art that a dosage range will vary depending on the particular corrin derivative being used.

For example, the corrin derivative can be administered to a subject in an amount as follows: about 0.1 mg/kg to 100 mg/kg weight of the subject, about 0.5 to 5 mg/kg weight of a subject, about 5 to 10 mg/kg weight of a subject, about 10 to 15 mg/kg weight of a subject, about 15 to 20 mg/kg weight of a subject, about 20 to 25 mg/kg weight of a subject, about 25 to 30 mg/kg weight of a subject, about 30 to 35 mg/kg weight of a subject, about 35 to 40 mg/kg weight of a subject, about 40 to 45 mg/kg weight of a subject, about 45 to 50 mg/kg weight of a subject, about 50 to 55 mg/kg weight of a subject, about 55 to 60 mg/kg weight of a subject, about 60 to 65 mg/kg weight of a subject, about 65 to 70 mg/kg weight of a subject, about 70 to 75 mg/kg weight of a subject, about 75 to 80 mg/kg weight of a subject, about 80 to 85 mg/kg weight of a subject, about 85 to 90 mg/kg weight of a subject, about 90 to 95 mg/kg weight of a subject, about 95 to 100 mg/kg weight of a subject, about 2 to 10 mg/kg weight of a subject, about 0.1 to 4 mg/kg weight of a subject, about 0.1 to 0.5 mg/kg weight of a subject, about 0.5 to 1.0 mg/kg weight of a subject, about 1.0 to 1.5 mg/kg weight of a subject, about 1.5 to 2.0 mg/kg weight of a subject, about 2.0 to 2.5 mg/kg weight of a subject, about 2.5 to 3.0 mg/kg weight of a subject, about 3.0 to 3.5 mg/kg weight of a subject, about 3.5 to 4.0 mg/kg weight of a subject, about 4.0 to 4.5 mg/kg weight of a subject, about 4.5 to 5.0 mg/kg weight of a subject, about 5.0 to 5.5 mg/kg weight of a subject, about 5.5 to 6.0 mg/kg weight of a subject, about 6.0 to 6.5 mg/kg weight of a subject, about 6.5 to 7.0 mg/kg weight of a subject, about 7.0 to 7.5 mg/kg weight of a subject, about 7.5 to 8.0 mg/kg weight of a subject, about 8.0 to 8.5 mg/kg weight of a subject, about 8.5 to 9.0 mg/kg weight of a subject, about 9.0 to 9.5 mg/kg weight of a subject, about 9.5 to 10.0 mg/kg weight of a subject, about 0.1 to 2 mg/kg weight of a subject, about 2 to 4 mg/kg weight of a subject, about 4 to 6 mg/kg weight of a subject, about 6 to 8 mg/kg weight of a subject, about 8 to 10 mg/kg weight of a subject, about 10 to 12 mg/kg weight of a subject, about 12 to 14 mg/kg weight of a subject, about 14 to 16 mg/kg weight of a subject, about 16 to 18 mg/kg weight of a subject, about 18 to 20 mg/kg weight of a subject, about 0.5 mg/kg weight of the subject, 2 mg/kg weight of the subject, 10 mg/kg weight of the subject, about 0.5 mg/kg to 100 mg/kg weight of the subject, about 0.5 to 10 mg/kg weight of a subject, about 0.1 mg/kg to 20 mg/kg weight of a subject, about 500 mg for a subject weighing less than 60 kg, 750 mg for a subject weighing between 60-100 kg, 1000 mg for a subject weighing more than 100 kg, about 0.1 gram per dose, about 0.5 gram per dose, about 1 gram per dose, about 2 gram per dose, about 3 gram per dose, about 4 gram per dose, about 5 gram per dose, about 6 gram per dose, about 7 gram per dose, about 8 gram per dose, about 9 gram per dose, about 10 gram per dose, about 11 gram per dose, about 12 gram per dose, about 13 gram per dose, about 14 gram per dose, about 15 gram per dose, about 16 gram per dose, about 17 gram per dose, about 18 gram per dose, about 19 gram per dose or about 20 gram per dose.

The corrin derivative can be administered to a subject in an amount and for a time (e.g. length of time and/or multiple times) sufficient to inhibit NOS. In an embodiment, a corrin derivative can be administered to a subject continuously, or intermittently, daily, weekly, monthly and/or yearly, in single or multiple times per day/week/month/year, depending on need. For example, in one embodiment, a corrin derivative can initially be administered in high dosage (e.g., up to 15 grams/day) every day for several days, one week or up to a month depending on need. Thereafter, the corrin derivative can be administered at a lower dosage in a maintenance regimen for as long as needed.

Another aspect of the invention relates to screening assays and methods that can be used to detect and identify compounds that bind and/or inhibit NOS. Specifically, NOS inhibitors can be identified by the ability of the compound to bind to NOS and/or the ability to inhibit NOS activity. Assays for NOS activity (e.g., binding) using a NOS protein such as NOS1, NOS2 and/or NOS3 are suitable for use in high through-put screening methods.

In one embodiment, the screening assay comprises mixing NOS with a compound of interest. After mixing under conditions that allow association of the compound to NOS, the mixture is analyzed to determine if the compound is bound to NOS. Binding compounds are identified as being able to bind to NOS. Alternatively or consecutively, NOS activity can be directly assessed as a means for identifying agonists/antagonists/stimulators/inhibitors of NOS activity.

In another embodiment, the present invention provides methods of screening for a compound that inhibits NOS by adding the compound of interest to a screening assay wherein NOS is converting L-arginine to L-citrulline and nitric oxide. The ability of the compound of interest to inhibit the conversion of L-arginine to L-citrulline determines the NOS inhibitory ability of the compound.

In an embodiment of the invention, a screening assay to identify compounds that inhibit NOS comprises:
 a) contacting the compound of interest to a solution containing radio-labeled-L-arginine and NOS (e.g., NOS1, NOS2 and/or NOS3);
 b) adding excess non-labeled L-citrulline to the solution;
 c) detecting the amounts of radio-labeled-L-arginine and radio-labeled-citrulline present;
 d) calculating the percent inhibition of NOS by the compound of interest as a ratio of radio-labeled-L-arginine to radio-labeled-citrulline; and thereby screening a compound of interest for inhibition of NOS.

Detection of NOS inhibition can be carried out using direct and/or indirect screening assays, including but not limited to the screening assays discussed above.

NOS proteins which can be used in the above assays include, but are not limited to, an isolated NOS protein, a fragment of a NOS protein, a cell that has been altered to express a NOS protein, or a fraction of a cell that has been altered to express a NOS protein. Further, the NOS protein can be the entire NOS protein or a defined fragment of the NOS protein. It will be apparent to one of ordinary skill in the art that so long as the NOS protein can be assayed for agent binding, e.g., by a shift in molecular weight or activity, the present assay can be used.

The method used to identify whether a compound binds to a NOS protein will be based primarily on the nature of the NOS protein used. For example, a gel retardation assay can be used to determine whether an agent binds to NOS or a fragment thereof. Alternatively, immunodetection and biochip technologies can be adopted for use with the NOS protein. A skilled artisan can readily employ numerous art-known techniques for determining whether a particular agent binds to a NOS protein.

Compounds that are assayed in the above methods can be randomly selected or rationally selected or designed. As used herein, a compound is said to be randomly selected when the compound is chosen randomly without considering the specific sequences of the NOS protein. An example of randomly selected agents is the use of a chemical library or a peptide combinatorial library, or a growth broth of an organism or plant extract.

As used herein, a compound is said to be rationally selected or designed when the compound is chosen on a nonrandom basis that takes into account the sequence of the target site and/or its conformation in connection with the compound's action. For example, compounds can be rationally selected or rationally designed by utilizing the peptide sequences that make up the NOS protein. Alternatively, a rationally selected compound can be an analog of the cobalamins or cobinamides used in the present invention. Also, a rationally selected compound can be identified with computer models (see infra, FIGS. 7 and 8) as computer modeling with NOS can help predict the ability of agents to bind and/or associate with NOS.

The compounds tested in the methods of the present invention can be, as examples, peptides, small molecules, and vitamin derivatives, as well as carbohydrates. A skilled artisan can readily recognize that there is no limit as to the structural nature of the agents used in the present screening method. One class of compounds of the present invention is corrin derivatives. A subclass of compounds of the present invention is cobalamins and/or cobinamides.

The present invention includes pharmaceutical compositions comprising pharmaceutically effective amounts of a corrin derivative. The pharmaceutical compositions preferably include suitable carriers which include any material which when combined with the molecules of the invention (i.e, a corrin derivative) retain the molecule's activity, and is non-reactive with the subject's immune system. These carriers include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, phosphate buffered saline solution, water, emulsions (e.g. oil/water emulsion), salts or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances and polyethylene glycol. Other carriers may also include sterile solutions; tablets, including coated tablets and capsules. Typically such carriers contain excipients such as starch, milk, sugar (e.g. sucrose, glucose, maltose), certain types of clay, gelatin, stearic acid or salts thereof, magnesium or calcium stearate, talc, vegetable fats or oils, gums, glycols, or other known excipients. Such carriers may also include flavor and color additives or other ingredients. Compositions comprising such carriers are formulated by well known conventional methods. Such compositions may also be formulated within various lipid compositions, such as, for example, liposomes as well as in various polymeric compositions, such as polymer microspheres.

An embodiment of the pharmaceutical composition of the invention comprises an effective amount of a corrin derivative that blocks NOS activity. In an embodiment of the invention, the pharmaceutical composition comprises a cobalamin or cobinamide. In a preferred embodiment of the invention, the pharmaceutical composition comprises dicyanocobinamide.

The pharmaceutical compositions of the invention can be useful for treating diseases or medical conditions associated with elevated NOS levels and/or inflammatory and/or neurological diseases or medical conditions.

Further details on techniques for formulation and administration may be found in the latest edition of Remington's Pharmaceutical Sciences (Ed. Maack Publishing Co, Easton, Pa.).

In a further embodiment of the invention, the present invention provides kits (i.e., a packaged combination of reagents with instructions) containing the corrin derivatives of the invention useful for blocking NOS activity and/or for treating an inflammatory or neurological disease or medical condition or for treating a condition associated with elevated NOS levels.

The kit can contain a pharmaceutical composition that includes one or more agents, for example, a corrin derivative of the invention and an acceptable carrier or adjuvant, e.g., pharmaceutically acceptable buffer, such as phosphate-buffered saline, Ringer's solution and dextrose solution. It may further include other materials desirable from a commercial and user standpoint, including other buffers, diluents, filters, needles, syringes, and package inserts with instructions for use. The agents may be provided as dry powders, usually lyophilized, including excipients that upon dissolving will provide a reagent solution having the appropriate concentration.

The kit comprises a container with a label and/or instructions. Suitable containers include, for example, bottles, vials, and test tubes. The containers can be formed from a variety of materials such as glass or plastic. The container can have a sterile access port (for example the container can be an intravenous solution bag or a vial having a stopper pierceable by a needle such as a hypodermic injection needle). The container can hold a pharmaceutical composition such as a pharmaceutical composition having an agent that is effective for blocking NOS activity.

In a further embodiment, corrin derivatives can be used as a blood additive to preserve blood stored ex vivo for future transfusion into a subject. Addition of the corrin derivative can prevent production of NO by leukocytes in the blood, thereby inhibiting the deleterious activities of NO to the other components in the blood.

The following examples are presented to illustrate the present invention and to assist one of ordinary skill in making and using the same. The examples are not intended in any way to otherwise limit the scope of the invention.

EXAMPLES

The examples, which are intended to be purely exemplary of the invention and should therefore not be considered to limit the invention in any way, also describe and detail aspects and embodiments of the invention discussed above. The examples are not intended to represent that the experiments below are all or the only experiments performed. Efforts have been made to ensure accuracy with respect to numbers used (e.g., amounts, temperature, etc.) but some experimental errors and deviations should be accounted for. Unless indicate otherwise, parts are parts by weight, molecular weight is weight average molecular weight, temperature is in degrees Centigrade, and pressure is at or near atmospheric.

While the present invention has been described with reference to the specific embodiments thereof, it should be understood by those skilled in the art that various changes may be made and equivalents may be substituted without departing from the true spirit and scope of the invention. In addition, many modifications can be made to adapt a particular situation, material, composition of matter, process, process step or steps, to the objective, spirit and scope of the present inven-

Example 1

Cobalamins and Cobinamides Inhibit Nitric Oxide Synthase Enzymatic Activity

Methods and Materials

We prepared highly purified, recombinant NOS1 and NOS2 (24,25). Recombinant bovine NOS3 was purchased from Cayman (Ann Arbor, Mich.). Tetrahydrobiopterin and carboxy-PTIO {2-(4-Carboxyphenyl)-4,4,5,5-tetramethylimidazoline-1-oxyl-3-oxide (potassium salt)} were from Alexis (San Diego, Calif.). 14-C-labeled L-arginine and 14-C-labeled citrulline were from Amersham/GE Healthcare (Waukesha, Wis.). All other reagents were from Sigma-Aldrich (St. Louis). The J774 and Raw 264 mouse macrophage cell lines were from the ATCC (Manassas, Va.). The cells were incubated in Dulbecco's modified Eagle medium (DMEM) or RPMI-1640 with 10% fetal bovine serum (26). NO levels were measured using a "Nitric Oxide Analyzer" (Sievers, Boulder, Colo.) or using diaminofluorescein-FM (4-amino-5-methylamino-2',7'-difluorofluorescein) from Invitrogen-Molecular Probes.

Briefly, cells were treated with 500 units/ml of murine interferon-gamma for 24 hours, incubated with 10 uM DAF-FM for 30 minutes, and washed. Then the cells were then assessed for fluorescence in a platereader fluorimeter. The degree of NO formation is proportional to the degree of fluorescence of DfAF-FM. To determine NOS activity, we incubated 14-C-labeled-L-arginine was at 37° C. with 5 nM recombinant NOS1, NOS2 or NOS3 with HEPES buffer, dithiothreitol, tetrahydrobiopterin, FAD, and NADPH in the absence or presence of different concentrations of the compound in question for 60 minutes (27, 28). The reaction was stopped by adding excess L-citrulline, after which 14-C-labeled L-arginine was separated from 14-C-labeled citrulline using a Dowex-50 column (with the 14-C-labeled L-arginine being bound to the Dowex-50, and 14-C-labeled citrulline eluting free from the column). Radioactivity was determined with a scintillation counter, and percentage NOS inhibition was calculated. We determined that none of the compounds quenched detection of the radioactivity. Spectroscopy was determined using a Hitachi U2010 spectrometer (San Jose, Calif.) as noted before (17, 24, 25).

Results

Figure 2:
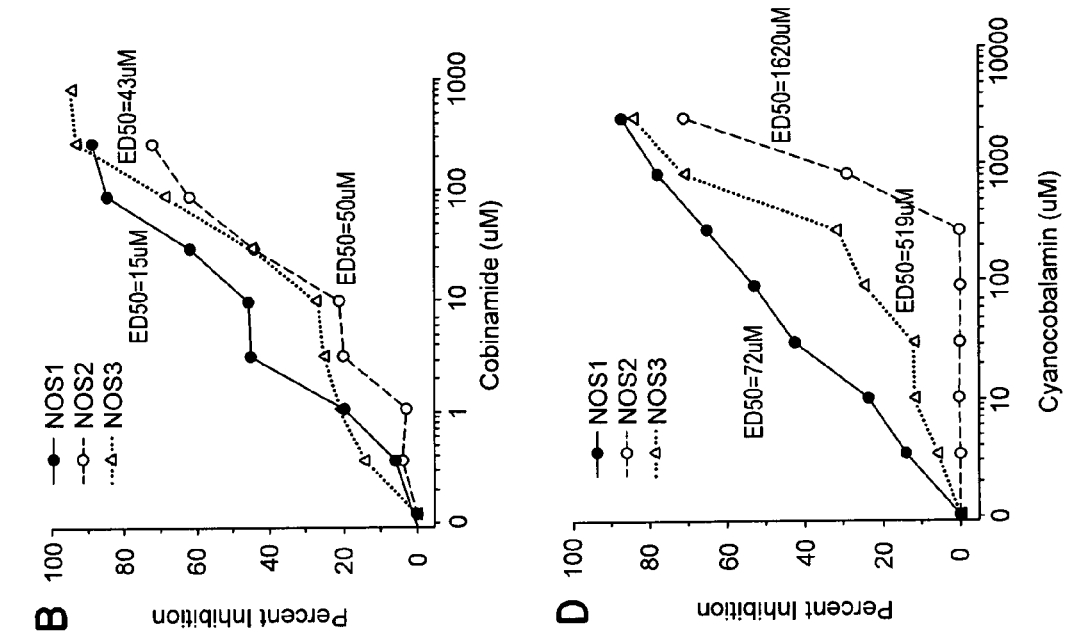
FIG. 2 demonstrates the inhibition of NOS1, NOS2, and NOS3 enzymatic by cobinamides and cobalamins. The enzymatic activity of purified NOS1, NOS2, or NOS3 to convert radiolabeled L-arginine to L-citrulline was assessed in presence or absence of different concentrations of (A) hydroxocobalamin, (B) cobinamide, (C) dicyanocobinamide, or (D) cyanocobalamin. Results are expressed as percent inhibition. The effective dose for 50% inhibition (ED50) is displayed.
Figure 2:
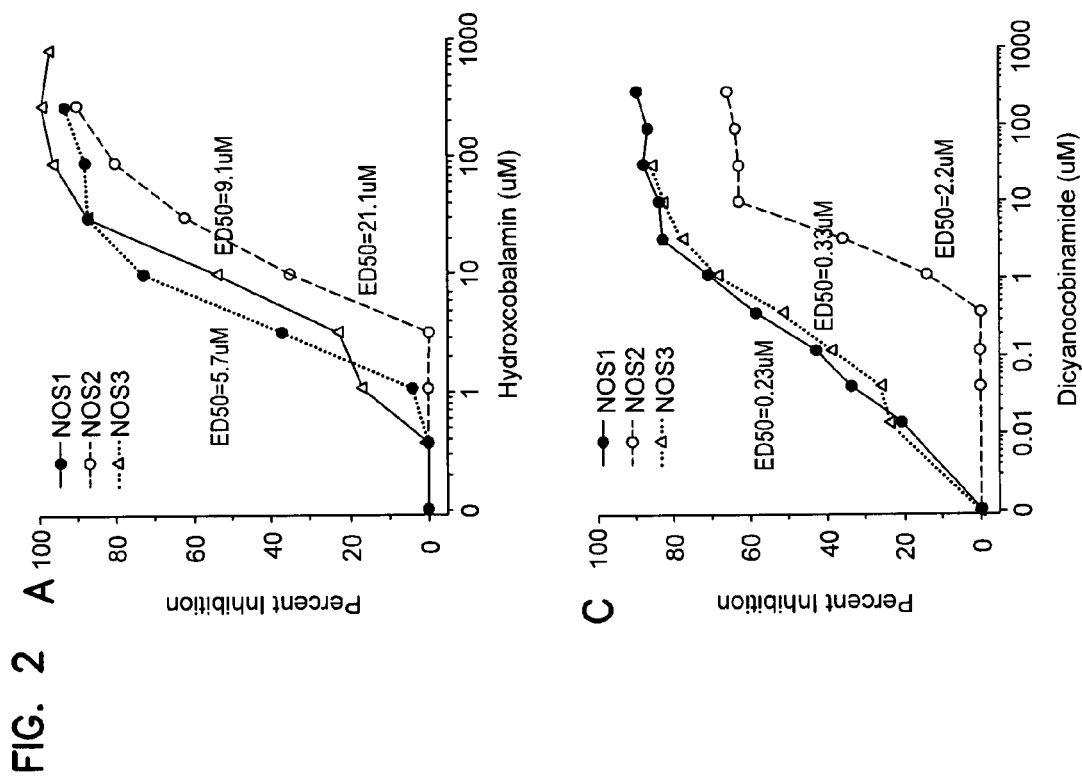
Figure 3:
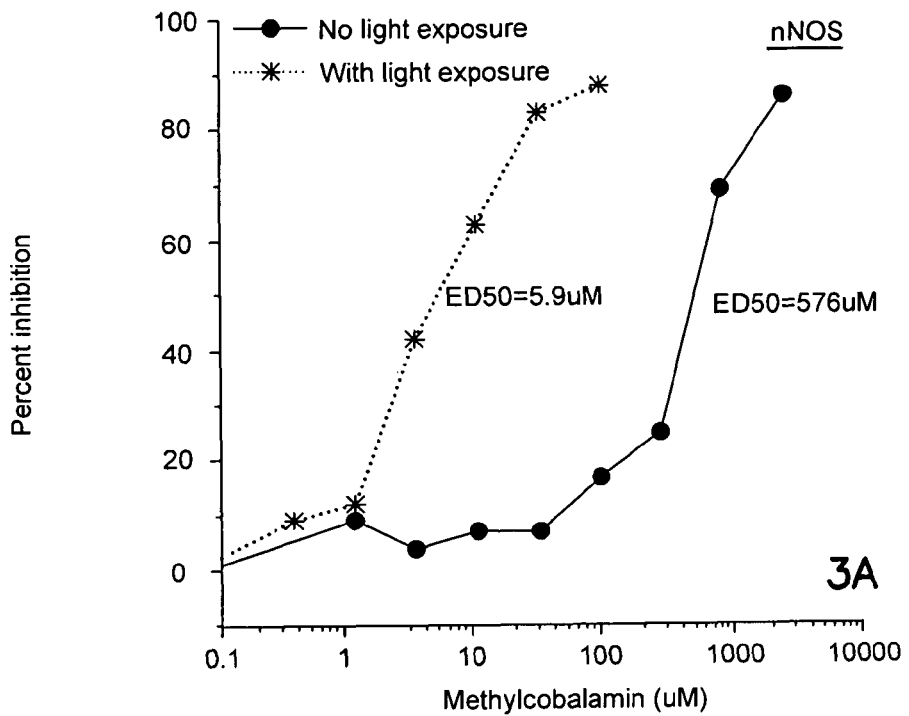
FIG. 3 demonstrates the influence of light on inhibition of purified, recombinant human nNOS (NOS1) and iNOS (NOS2) by methylcobalamin and adenosylcobalamin. The effect of methylcobalamin (not exposed to light or exposed to light) on nNOS is shown in FIG. 3A; its effect on iNOS is shown in FIG. 3B. The effect of adenosylcobalamin (not exposed to light or exposed to light) on nNOS is shown in FIG. 3C; its effect on iNOS is shown in FIG. 3D. The agents were protected from light or exposed to light for 60 minutes. The enzyme assays were done in near-dark conditions (as low light as possible). Light removes the methyl- or adenosyl-group from the agent resulting in hydroxocobalamin. Methylcobalamin and adenosylcobalamin have very little NOS inhibitory activity, but after light-induced change to hydroxocobalamin, they actively inhibit NOS1 and NOS2 activity.
Figure 3:
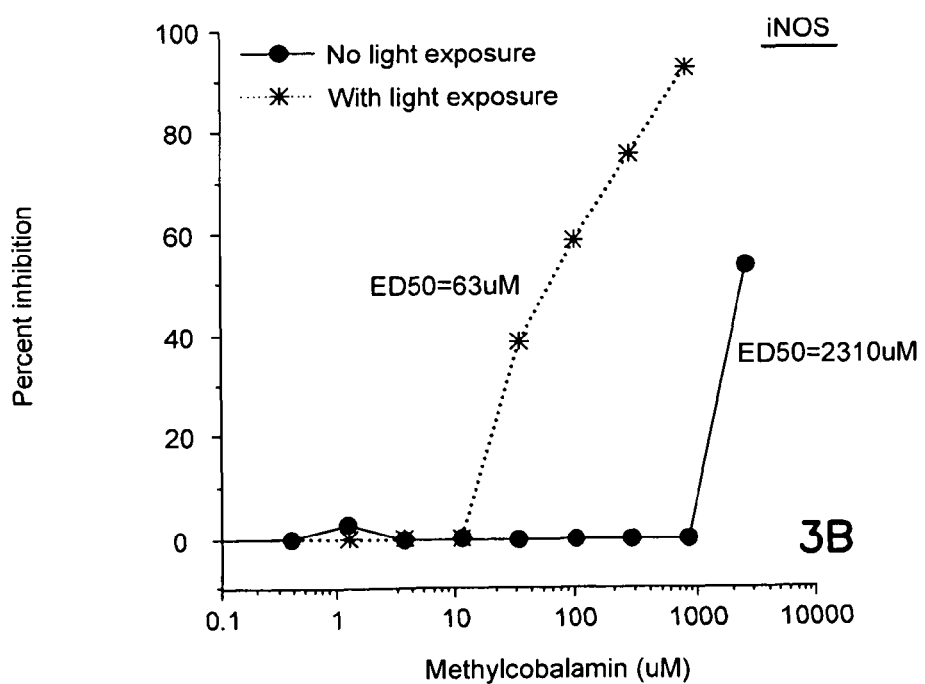
Figure 3:
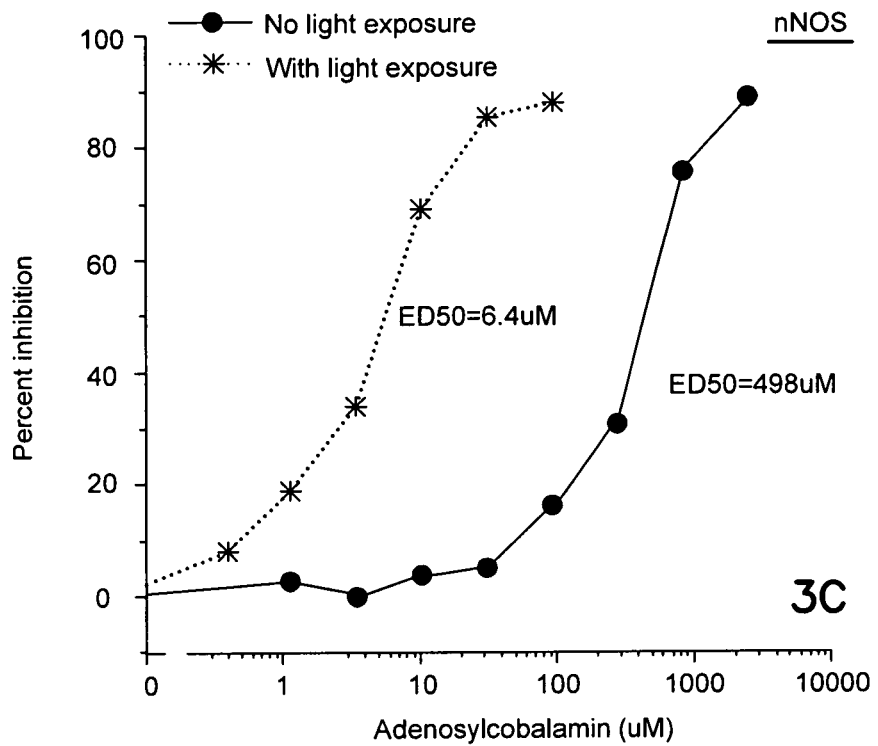
Figure 3:
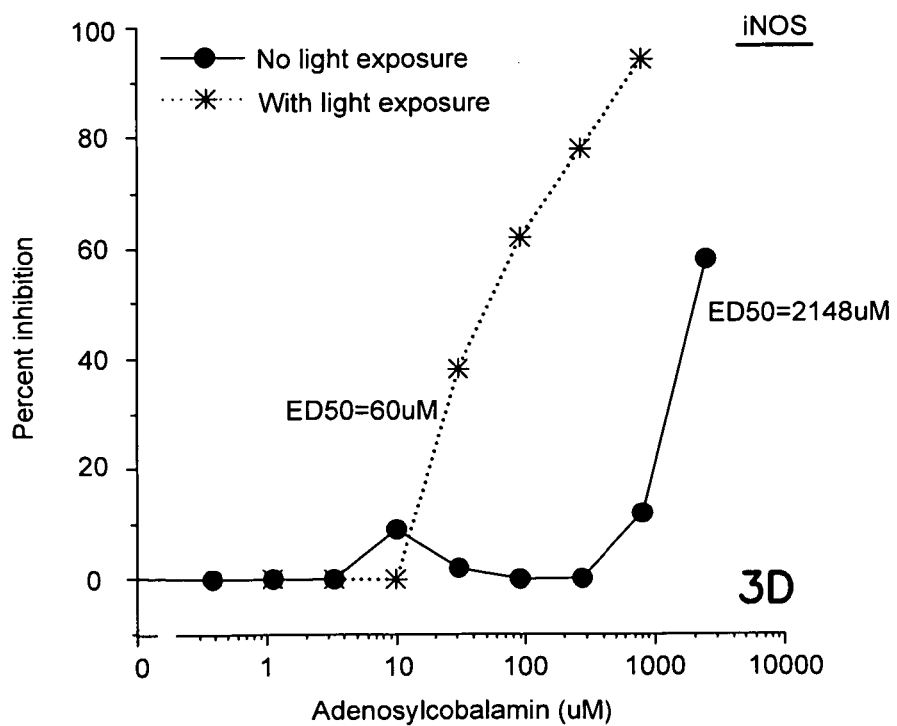

We first sought to determine is the various corrin-related compounds had direct effects on the catalytic activity of NOS. Using 14-C-labeled L-arginine, purified recombinant NOS1 or NOS2 and NOS co-factors, we tested the compounds for their abilities to influence conversion of 14-C-L-arginine to 14-C-L-citrulline. Hydroxocobalamin (OH-Cbl), cobinamide (Cbi), and dicyanocobinamide ($CN_2$-Cbi) were potent NOS1 and NOS2 inhibitors, while cyanocobalamin had much less activity (FIG. 2). In general, NOS1 was inhibited more actively than was NOS2, but both were inhibited by the agents. Methylcobalamin and adenosylcobalamin had very little ability to inhibit NOS activity, but light illumination of these two compounds {a process that liberates the methyl and adenosyl groups from cobalamin, generating OH-Cbl (17)} "activated" them so that they now had inhibitory activity (comparable to native OH-Cbl) (FIG. 3). Table 1 summarizes the inhibitions.

TABLE 1

Inhibition of iNOS and nNOS and eNOS by cobalamins and cobinamides.

| | ED50 (uM) | | |
|---|---|---|---|
| | NOS1 | NOS2 | NOS3 |
| Hydroxocobalamin | 5.7 | 21.1 | 9.1 |
| Cobinamide | 15.0 | 50.0 | 43.0 |
| Dicyanocobinamide | 0.23 | 2.29 | 0.33 |
| Cyanocobalamin | 72.0 | 1620.0 | 519.0 |
| Carboxy-PTIO | 1360.0 | 1359.0 | — |
| Methylcobalamin (no light) | 576.0 | 231.0 | — |
| Methylcobalamin (with light) | 5.9 | 63.0 | — |
| Adenosylcobalamin (no light) | 498.0 | 2148.0 | — |
| Adenosylcobalamin (with light) | 6.4 | 60.0 | — |

Figure 4:
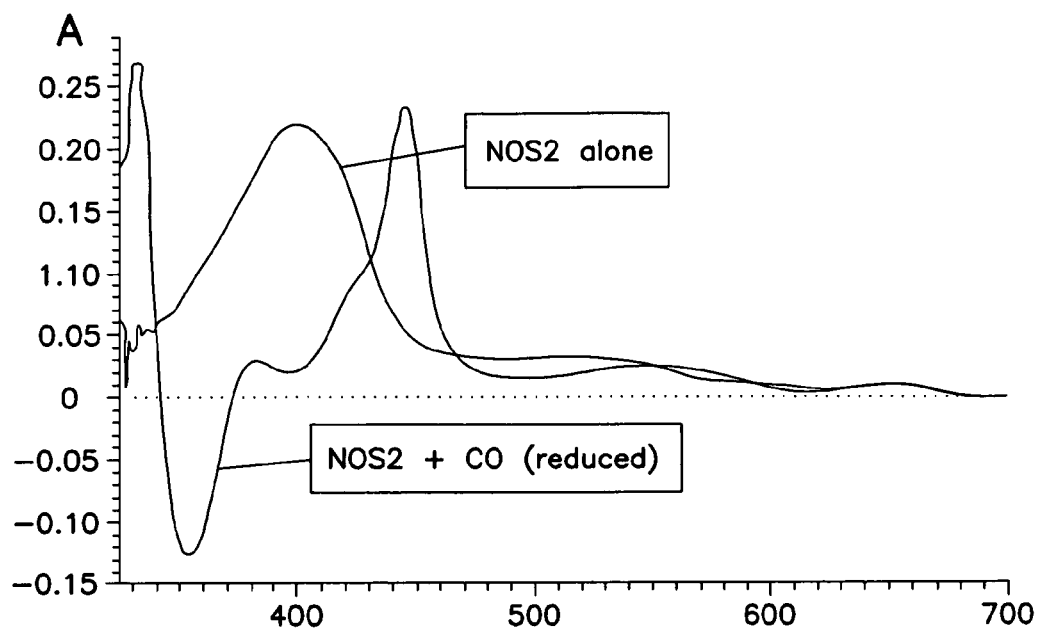
FIG. 4 demonstrates that dicyanocobinamide reacts directly with purified, recombinant NOS2. Oxygen reacts directly with the reduced iron of the heme group in NOS. Carbon monoxide (CO) (that simulates $O_2$ in binding to the reduced iron) was used to determine the influence of $CN_2$-Cbi on oxygen binding to NOS. The reaction of purified NOS2 with CO in a reduced state (dithionite) markedly changed the UV/Vis spectrum, with appearance of the typical CO-bound $Fe^{+2}$-heme peak at 445 nm (FIG. 4A). However, in the presence of $CN_2$-Cbi, there was no appearance of the 445 nm peak induced by CO in a reduced state (FIG. 4B). Similar findings were noted with OH-Cbl.
Figure 4:
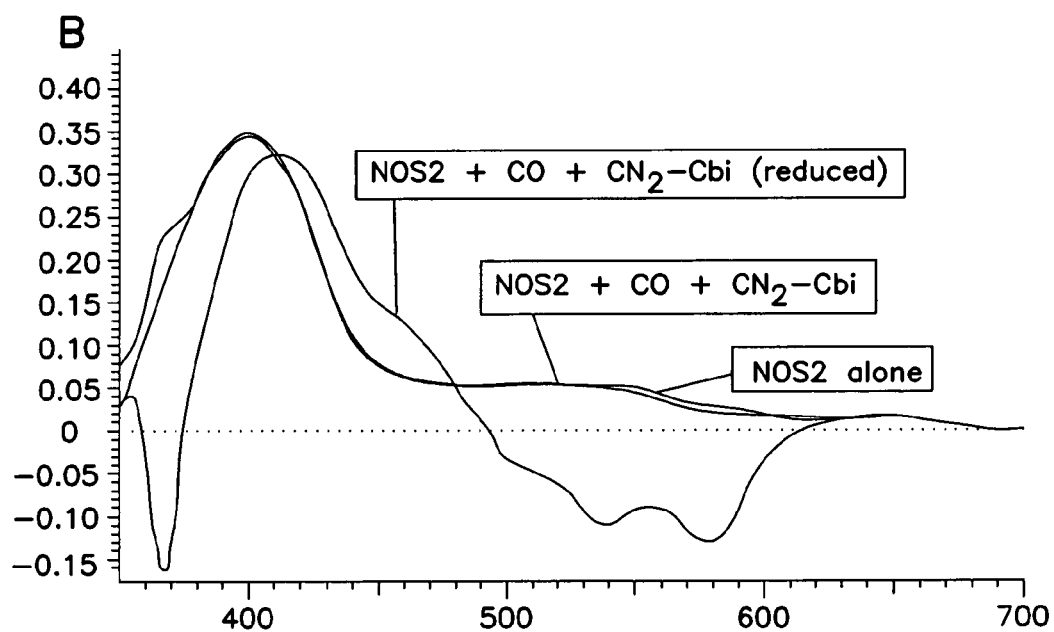

We examined the interactions of NOS1 and NOS2 with cobalamins and cobinamides by spectroscopy to determine if the compounds interacted directly with NOSs. FIG. 4 shows results for experiments with dicyanocobinamide. Under reduced conditions, oxygen binds to the iron of heme in NOS. Carbon monoxide (CO, which serves as an oxygen mimic) causes a marked change in the NOS spectrum under reduced conditions. As noted in FIG. 4, $CN_2$-Cbi markedly diminished the CO-induced spectral changes in NOS2, indicating that $CN_2$-Cbi likely blocks binding of CO to the NOS2 oxygenase domain under reduced conditions. This suggests that $CN_2$-Cbi-mediated inhibition of NOS2 activity is due to blocking of oxygen binding to heme, a step required for the NOS catalytic cycle. No one has ever demonstrated an interaction of a cobalamin or a cobinamide with NOS before.

Figure 5:
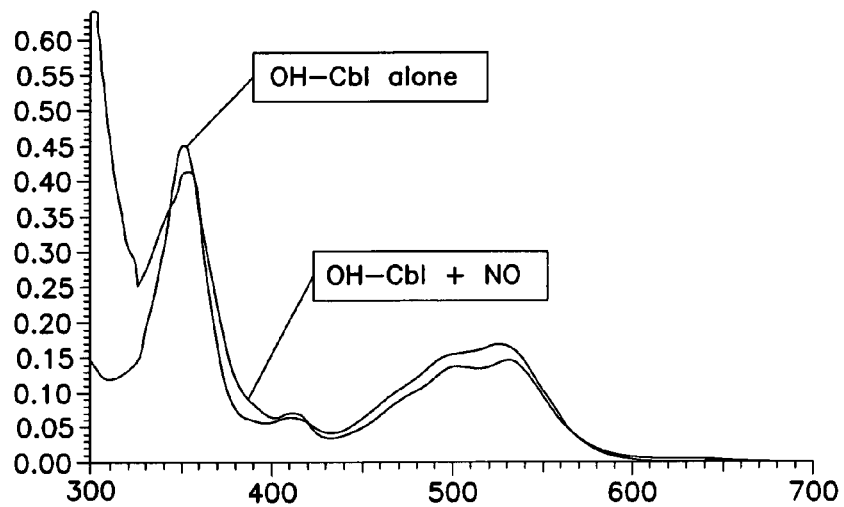
FIG. 5 demonstrates that hydroxocobalamin binds NO, but dicyanocobinamide does not. NO reacts with OH-Cbl as indicated by the change in the UV/Vis spectrum (shift of peak from 352 nm to 354-355 nm, and alteration in the 520 nm region). However, NO does not react with $CN_2$-Cbi (no change in spectrum).
Figure 5:
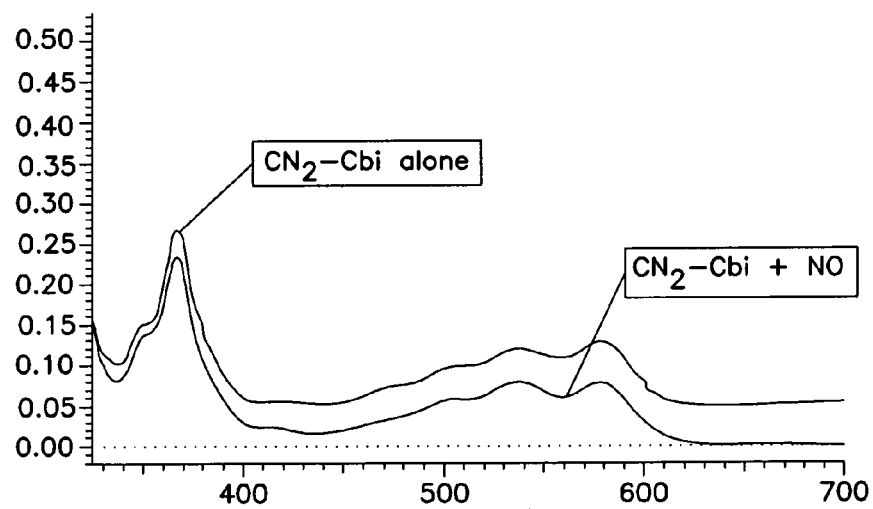

As noted above, OH-Cbl is known to directly bind NO to its cobalt and quench or scavenge the actions of NO (12-23). We tested the ability of $CN_2$-Cbi to interact with NO (FIG. 5). NO reacted with OH-Cbl as indicated by the change in the UV/visible spectrum (shift of peak from 352 nm to 354-355 nm, and alteration in the 520 nm region). However, NO did not react with $CN_2$-Cbi (essentially no change in its spectrum). Since $CN_2$-Cbi does not bind/quench NO, and carboxy-PTIO (a known NO binding-quenching compound) does not inhibit NOS (FIG. 3 and Table), we conclude that the NOS inhibitory actions of cobalamins and cobinamide are not related to NO binding.

Figure 6A:
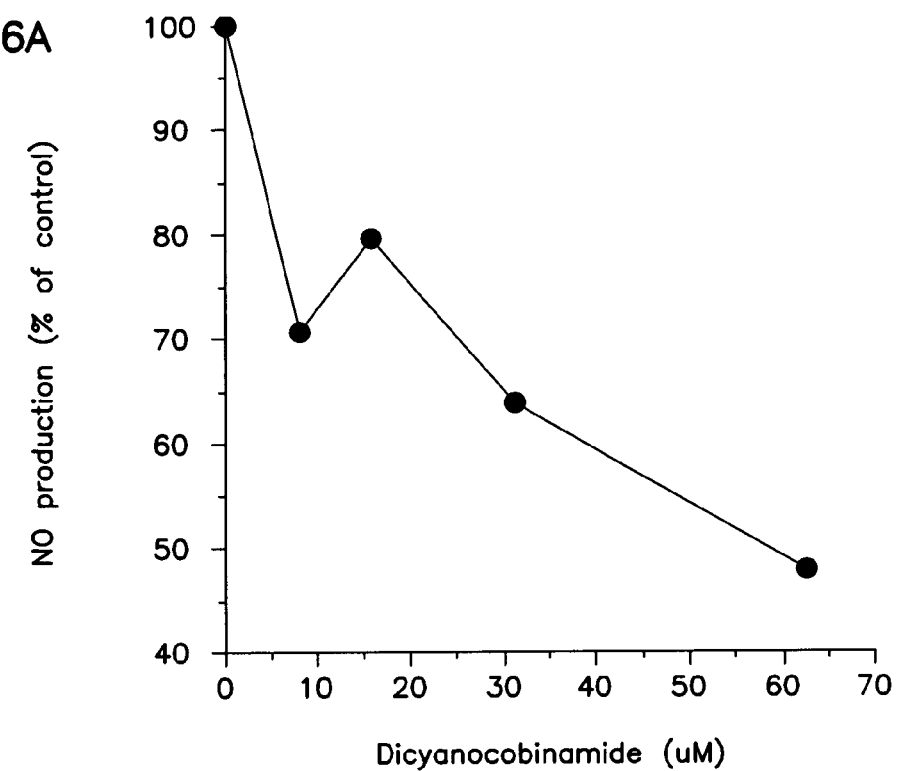
FIG. 6A demonstrates inhibition of NO formation by mouse macrophages (J774 cells). Cells of the mouse macrophage cell line J774 were incubated 3 days with 10 ng/ml endotoxin and 100 units/ml murine interferon gamma to activate the macrophage-like cells for NO production. The cultures also contained 0 to 62.5 uM dicyanocobinamide for the 3 days. At the end of the culture period, supernatant cell NO production was determined.
Figure 6B:
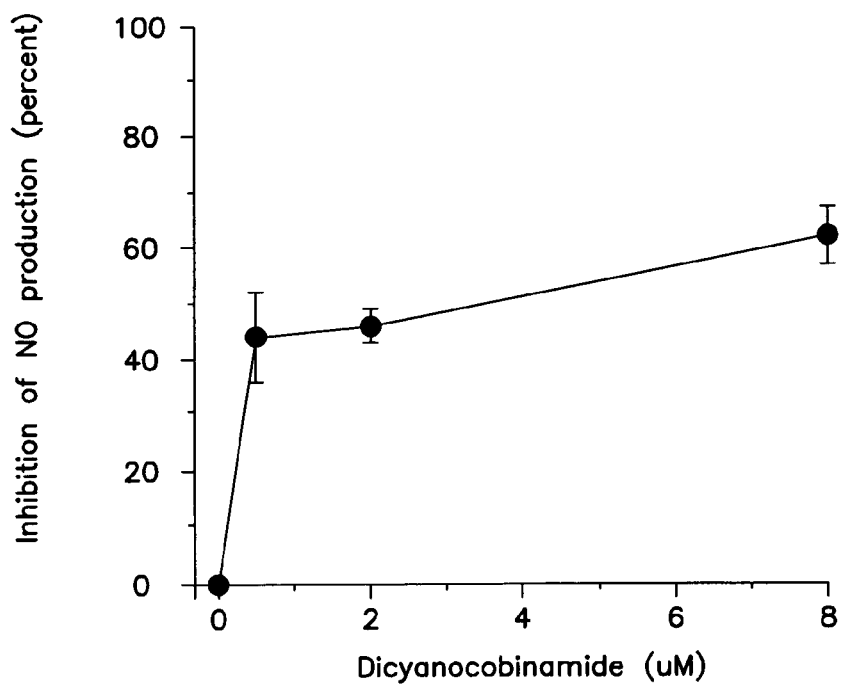
FIG. 6B demonstrates inhibition of NO formation by mouse macrophages (Raw 264 cells). Cells of the mouse macrophage cell line Raw 264 were incubated 24 hours with 100 units/ml murine interferon gamma to activate the macrophage-like cells for NO production. The cultures also contained 0, 0.5, 2.0, or 8.0 uM dicyanocobinamide for the entire culture period. At the end of the culture period the cells were assessed for NO production using DAF-MN and a fluorimeter. Results are expressed as percent inhibition. The error bars show the SEM.

Next, we tested the abilities of $CN_2$-Cbi to influence NO production by cells expressing NOS and producing NO. When we incubated $CN_2$-Cbi with cells of the mouse macrophage cell line J774 activated with interferon-gamma and endotoxin to produce NO, there was a dose-dependent inhibition of NO production (FIG. 6A). Additionally, when we incubated $CN_2$Cbi with cells of the mouse macrophage cell line Raw 264 activated with interferon-gamma to produce NO in vitro, there was a dose-dependent inhibition of NO production (FIG. 6B). This indicates that compounds of this class can inhibit NO production by NOS (primarily NOS2 in these macrophages) in living cells. While cobalamins have been previously noted to bind and quench the actions of preformed NO, we show here for the first time that a cobinamide can actually inhibit/block the enzymatic function of NOS and thus actual formation of NO.

Certain Cobalamins (e.g., OH-Cbl) and Cobinamides (e.g., Cbi) are able to bind and scavenge NO. Thus, these agents are able to bifunctionally inhibit the NOS/NO system by decreasing NOS activity and NO synthesis and quenching pre-made NO. Unlike, OH-Cbl and Cbi, we show that $CN_2Cbi$ does not bind NO, but it very potently inhibits NOS activity.

Example 2

Molecular modeling studies of docking of cobalamin structures with NOS1 and NOS2 isoforms were done in InsightII (Accelrys) using structures from PDB entries P_1DWW (NOS2) and P_1ZVL (NOS1). Side chains were individually torsioned to remove intramolecular bumps with cobalamin while monitoring local energies (Van der waals and Coulomb) to eliminate unrealistic conformations. Single bonds in cobalamin were torsioned to reposition dimethylbenzimidazole for reduced steric effects. No attempt to estimate binding energies was made because of the lack of a generally available force field for cobalamins/corrins, and because of the likelihood that the lowest energy configurations would require several layers of side chain adjustments.

Figure 7:
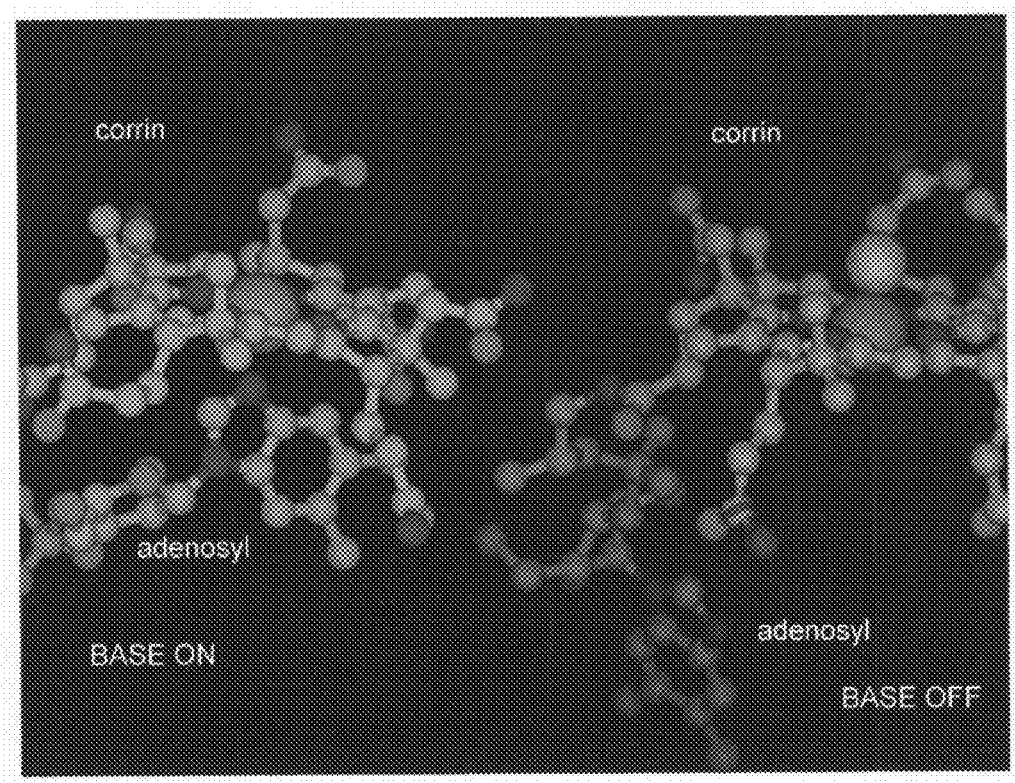
FIG. 7 shows molecular models of structures of adenosylcobalamin in the base-on and base-off configurations showing the positions of the corrin ring and the dimethylbenzimidazole moiety. The purple spheres represent the vanderwaals surface of the cobalt atom. The structure of the base-off form was taken from the structure glutamate mutase reported by Reitzer et al (PDB entry 1cb7); in this structure the ligand trans to the methyl axial ligand is a histidyl residue (not shown) supplied by the protein. The base-on form shown was taken from the structure of transcobalamin reported by Wuerges et al (PDB entry 2bb5). The axial ligand trans to dimethylbenzimidazole is again a histidyl residue supplied by the protein. Slight differences in the planarity of the corrins include movement of the cobalt towards dimethylbenzimidazole in the base-on configuration. Considerable flexibility in the molecule exists, making many other orientation of the base possible.
Figure 8:
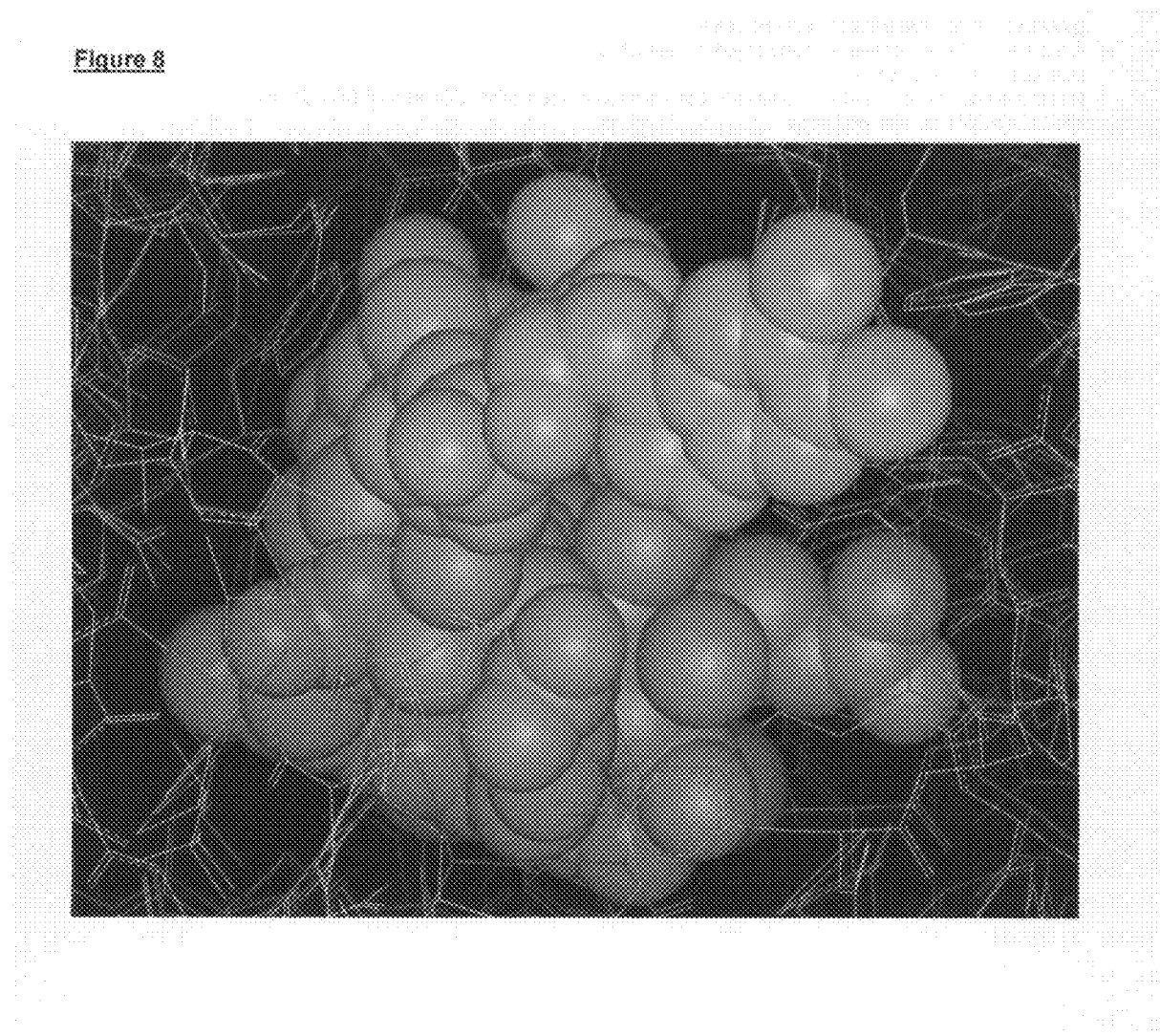
FIG. 8 shows docking of a base-off form of cobalamin in the heme pockets of iNOS (dark blue) and nNOS (cyan), illustrating the extent of the ligand binding cavity relative to the size of cobalamin. Heme is shown in red and cobalamin in purple. The very large substrate binding pocket accommodates surprisingly large ligands, including porphyrins (similar in size and shape to the corrin shown here). The insertion of cobalamin into the heme pocket is ultimately limited by a beta sheet near V567 (nNOS); the configuration shown generates a 0.4 A bump with the valine side chain in the crystal structure from PDB P_1ZVL, and represents the approximate limit of insertion of cobalamin assuming slight rearrangements in the backbone. A similar configuration with about 80% overlap of the corrin and heme can be obtained without backbone or unrelaxable side chain bumps. Slight torsioning of some active site residue side chains and repositioning of the DMBzI moeity, visible as rings at the upper right, was necessary.

To explore potential mechanisms of the NOS-corrin interactions, we used molecular modeling investigations with manual computer-assisted docking analysis (FIGS. 7 and 8). Cobalamins exist in aqueous solution in two main conformations, 'base-on' and 'base-off'; in the 'base-on' conformation the dimethylbenzimidazole moiety provides an axial ligand to the cobalt atom (FIG. 7). As shown in FIG. 8, there is enough space in the heme and substrate binding pocket of NOS1 and NOS2 to accommodate cobalamin in the 'base-off' conformation. It was necessary to adjust the conformation of binding site residues and ligand to allow ligand binding, but these adjustments do not come at the expense of large amounts of energy. The critical point revealed by docking exercises is that a very large interaction surface between base-off cobalamin and NOS (~800 $A^2$) can be obtained despite the high degree of exposure of the dimethylbenzimidazole moiety to solvent water. The complexity and scale of the binding region, coupled with the fact that adjustments in side chain orientation are not only likely but necessary to allow the cobalamin to fit, make attempts to define specific interactions within the pocket unreliable without further information. The large interaction surface accounts for the high affinity of nNOS for cobalamins. Small differences in pocket geometry provide slightly more space in nNOS than in iNOS (FIG. 7), which may account for NOS1's generally higher affinity for cobalamins. The effect of axial ligands on affinity suggests strongly that specific interactions within the pocket are important, and that these interactions account for part of the specificity for cobalamins based on axial ligation. Hydrogen bonds and metal-ligand bonds may both contribute; numerous groups are available for H bond formation in the pocket, including the groups involved in binding arginine. There are no active site histidyl residues available to bond to cobalt. However, other residues may supply a ligand, including a group of tryptophan residues surrounding the heme pocket. It is unlikely that cobalamins bind to NOS initially in the base-off state. The fraction of base-off molecules in a solution of hydroxocobalamin is so low (a few parts of in $10^8$) that binding would be too slow to account for the observed results. It is likely that initial weak binding occurs in the base-on state, which can be docked partially into the heme pocket with the corrin at an ~45 degree angle to the heme (not shown). Intermediate weakly bound states could provide a mechanism to reach the base-off state, allowing reasonably rapid binding of cobalamins that are essentially all in the base-on state in solution.

These evaluations indicated that the corrins can physically access the unusually large heme and substrate binding pocket of NOS. The binding appears to be best in the base-off conformation of the lower axial ligand dimethylbenzimidazole, with binding being facilitated by heme ring-corrin ring interactions and possibly by hydrogen bonding to arginine-binding groups in the active site pocket. The total base-off structure of $CN_2$-Cbi and the great potential of OH-Cbl to hydrogen-bond in the pocket help explain their low ID50s for inhibition. The slightly larger active site pocket of NOS1 compared to NOS2 and NOS3 likely explains the lower ID50s for NOS1.

Our structural modeling and spectroscopy studies indicate the NOS inhibition by these cobalamins and cobinamides is likely mediated by approximation of the agent to the NOS heme in active site. The active site pocket is large and accommodates the agent. The greater ability to inhibit NOS1 than NOS2 appears to be structurally based—the NOS1 active site pocket is larger than the NOS2 pocket. As noted, $CN_2Cbi$ is clearly the most potent inhibitor. Absence of the lower axial ligand (essentially having a continuous "base-off" configuration) enhances access to the NOS heme. Based on OH-Cbl's inhibitory ability and structural modeling, it appears that hydrogen bonding between the polar hydroxyl group of OH-Cbl and NOS contribute significantly to the OH-Cbl-NOS binding. Absence of a polar upper axial ligand in CN-Cbl and a "base-on" configuration likely explains the poor ability of CN-Cbl to inhibit NOS. Other researchers have reported inhibition of NOS by certain heme derivatives such as ferriprotoporphyrin IX or cobalt protoporphyrin (29-31).

Example 3

NOSs are heme-containing flavoproteins that function as homodimers. NOSs catalyze the oxidation of L-arginine to NO and L-citrulline, with NADPH and oxygen serving as co-substrates. NOSs first hydroxylate terminal guanidino nitrogen of arginine to generate N-hydroxy-L-arginine (NOHA) as an enzyme-based intermediate. NOHA is then oxidized further by the enzyme to generate NO and L-citrulline. NOS flavins transfer NADPH-derived electrons to heme iron. This process enables heme to bind and activate oxygen in both steps of NO synthesis. Tetrahydrobiopterin, a required NOS cofactor, binds to NOS tightly near the heme and is necessary for the homodimer formation and interaction with L-arginine (2). In the absence of L-arginine, the oxidase function of NOS generates superoxide from oxygen. Superoxide can contribute to inflammation and tissue damage in disorders such as arthritis, vasculitis, nephritis, and reperfusion injury (32). These corrin NOS inhibitors would be expected to inhibit both NO and superoxide generation from NOS in order to treat inflammatory and/or neurological diseases or medical conditions.

REFERENCES

1. Alderton W K, Cooper C E, Knowles R G. Nitric oxide synthases: structure, function and inhibition. Biochemical Journal 357: 593-615, 2001.
2. Stuehr D J. Mammalian nitric oxide synthases. Biochim Biophys Acta 1411: 217-230, 1999.
3. Moncada S, Higgs A. The L-arginine-nitric oxide pathway. New England Journal of Medicine 329: 2002-2012, 1993.
4. Stamler J S, Singel D J, Loscalzo J. Biochemistry of nitric oxide and its redox-activated forms. Science 258: 1898-1902, 1992.
5. Weinberg J B. Nitric oxide production and nitric oxide synthase type 2 expression by human mononuclear phagocytes—a review [Review]. Molecular Medicine 4: 557-591, 1998.

6. Li J R, Billiar T R, Talanian R V, Kim Y M. Nitric Oxide Reversibly Inhibits Seven Members Of the Caspase Family Via S-Nitrosylation. Biochemical & Biophysical Research Communications 240: 419-424, 1997.
7. Mannick J B, Hausladen A, Liu L M, Hess D T, Zeng M, Miao Q X, Kane L S, Gow A J, Stamler J S. Fas-induced caspase denitrosylation. Science 284: 651-654, 1999.
8. Babu B R, Griffith O W. Design of isoform-selective inhibitors of nitric oxide synthase [Review]. Current Opinion in Chemical Biology 2: 491-500, 1998.
9. Hibbs J B, Jr, Taintor R R, Vavrin Z. Macrophage cytotoxicity: role for L-arginine deiminase and imino nitrogen oxidation to nitrite. Science 235: 473-476, 1987.
10. Hibbs J B, Jr, Taintor R R, Vavrin Z, Rachlin E M. Nitric oxide: a cytotoxic activated macrophage effector molecule [published erratum appears in Biochem Biophys Res Commun 1989 Jan. 31; 158(2):624]. Biochem Biophys Res Commun 157: 87-94, 1988.
11. Frick K K, Bushinsky D A. Metabolic acidosis stimulates RANKL RNA expression in bone through a cyclo-oxygenase-dependent mechanism. J Bone Miner Res 18: 1317-1325, 2003.
12. Greenberg S S, Xie J M, Zatarain J M, Kapusta D R, Miller M J S. Hydroxocobalamin (Vitamin B12a) Prevents and Reverses Endotoxin-Induced Hypotension and Mortality In Rodents—Role Of Nitric Oxide. Journal of Pharmacology & Experimental Therapeutics 273: 257-265, 1995.
13. Broderick K E, Singh V, Zhuang S, Kambo A, Chen J C, Sharma V S, Pilz R B, Boss G R. Nitric oxide scavenging by the cobalamin precursor cobinamide. J Biol Chem 280: 8678-8685, 2005.
14. van der Kuy P H, Merkus F W, Lohman J J, ter Berg J W, Hooymans P M. Hydroxocobalamin, a nitric oxide scavenger, in the prophylaxis of migraine: an open, pilot study. Cephalalgia 22: 513-519, 2002.
15. Kruszyna H, Magyar J S, Rochelle L G, Russell M A, Smith R P, Wilcox D E. Spectroscopic studies of nitric oxide (NO) interactions with cobalamins: reaction of NO with superoxocobalamin(III) likely accounts for cobalamin reversal of the biological effects of NO. J Pharmacol Exp Ther 285: 665-671, 1998.
16. Kikuchi M, Kashii S, Honda Y, Tamura Y, Kaneda K, Akaike A. Protective effects of methylcobalamin, a vitamin B12 analog, against glutamate-induced neurotoxicity in retinal cell culture. Invest Opthalmol V is Sci 38: 848-854, 1997.
17. Brouwer M, Chamulitrat W, Ferruzzi G, Sauls D L, Weinberg J B. Nitric oxide interactions with cobalamins: biochemical and functional consequences. Blood 88: 1857-1864, 1996.
18. Akaike A, Tamura Y, Sato Y, Yokota T. Protective effects of a vitamin B12 analog, methylcobalamin, against glutamate cytotoxicity in cultured cortical neurons. Eur J Pharmacol 241: 1-6, 1993.
19. Li C G, Rand M J. Effects of hydroxocobalamin and haemoglobin on NO-mediated relaxations in the rat anococcygeus muscle. Clin Exp Pharmacol Physiol 20: 633-640, 1993.
20. Jenkinson K M, Reid J J, Rand M J. Hydroxocobalamin and Haemoglobin Differentiate Between Exogenous and Neuronal Nitric Oxide In the Rat Gastric Fundus. European Journal of Pharmacology 275: 145-152, 1995.
21. Rochelle L G, Morana S J, Kruszyna H, Russell M A, Wilcox D E, Smith R P. Interactions between hydroxocobalamin and nitric oxide (NO)—Evidence for a redox reaction between NO and reduced cobalamin and reversible NO binding to oxidized cobalamin. Journal of Pharmacology & Experimental Therapeutics 275: 48-52, 1995.
22. Akaike A, Tamura Y, Sato Y, Yokota T. Protective effects of a vitamin B12 analog, methylcobalamin, against glutamate cytotoxicity in cultured cortical neurons. European Journal of Pharmacology 241: 1-6, 1993.
23. Sharma V S, Pilz R B, Boss G R, Magde D. Reactions of nitric oxide with vitamin B12 and its precursor, cobinamide. Biochemistry 42: 8900-8908, 2003.
24. Gao Y T, Smith S M, Weinberg J B, Montgomery H J, Newman E, Guillemette J G, Ghosh D K, Roman L J, Martasek P, Salerno J C. Thermodynamics of oxidation-reduction reactions in mammalian nitric oxide synthase isoforms. J Biol Chem 279: 18759-18766, 2004.
25. Newman E, Spratt D E, Mosher J, Cheyne B, Montgomery H J, Wilson D L, Weinberg J B, Smith S M, Salerno J C, Ghosh D K, Guillemette J G. Differential activation of nitric-oxide synthase isozymes by calmodulin-troponin C chimeras. J Biol Chem 279: 33547-33557, 2004.
26. Ghosh D K, Misukonis M A, Reich C, Pisetsky D S, Weinberg J B. Host response to infection: the role of CpG DNA in induction of cyclooxygenase 2 and nitric oxide synthase 2 in murine macrophages. Infect Immun 69: 7703-7710, 2001.
27. Weinberg J B, Misukonis M A, Shami P J, Mason S N, Sauls D L, Dittman W A, Wood E R, Smith G K, McDonald B, Bachus K E, Haney A F, Granger D L. Human mononuclear phagocyte inducible nitric oxide synthase (iNOS). Analysis of iNOS mRNA, iNOS protein, biopterin, and nitric oxide production by blood monocytes and peritoneal macrophages. Blood 86: 1184-1195, 1995.
28. Sharara A I, Perkins D J, Misukonis M A, Chan S U, Dominitz J A, Weinberg J B. Interferon (IFN)-alpha activation of human blood mononuclear cells in vitro and in vivo for nitric oxide synthase (NOS) type 2 mRNA and protein expression—possible relationship of induced NOS2 to the anti-hepatitis C effects of IFN-alpha in vivo. J Exp Med 186: 1495-1502, 1997.
29. Jozkowicz A, Dulak J. Effects of protoporphyrins on production of nitric oxide and expression of vascular endothelial growth factor in vascular smooth muscle cells and macrophages. Acta Biochim Pol 50: 69-79, 2003.
30. Lim M D, Lorkovic I M, Ford P C. NO and NO(x) interactions with group 8 metalloporphyrins. J Inorg Biochem 99: 151-165, 2005.
31. Wolff D J, Naddelman R A, Lubeskie A, Saks D A. Inhibition Of Nitric Oxide Synthase Isoforms By Porphyrins. Arch Biochem Biophys 333: 27-34, 1996.
32. Kumar V, Abbas A K, Fausto N. Pathologic basis of disease (ed Seventh). Philadelphia: Elsevier Saunders; 2005.
33. Forsyth J C, Mueller P D, Becker C E, Osterloh J, Benowitz N L, Rumack B H, Hall A H. Hydroxocobalamin as a cyanide antidote: safety, efficacy and pharmacokinetics in heavily smoking normal volunteers. Journal of Toxicology and Clinical Toxicology 31: 277-294, 1993.
34. Houeto P, Borron S W, Sandouk P, Imbert M, Levillain P, Baud F J. Pharmacokinetics of hydroxocobalamin in smoke inhalation victims. Journal of Toxicology—Clinical Toxicology 34: 397-404, 1996.
35. Stabler S P, Brass E P, Marcell P D, Allen R H. Inhibition of cobalamin-dependent enzymes by cobalamin analogues in rats. J Clin Invest 87: 1422-1430, 1991.
36. Li M, Vizzard M A, Jaworski D M, Galbraith R A. The weight loss elicited by cobalt protoporphyrin is related to decreased activity of nitric oxide synthase in the hypothalamus. J Appl Physiol 100: 1983-1991, 2006.

37. Stuehr D J. Enzymes of the L-Arginine to Nitric Oxide Pathway. J Nutr. 134:2748S-2751S, 2004.
38. Morris S M. Enzymes of Arginine Metabolism. J Nutr. 134:2743S-2747S, 2004.
39. Durante W, Johnson F K, Johnson R A. Arginase: A Critical Regulator of Nitric Oxide Synthesis and Vascular Function. Clin Exp Pharmacol Physiol. 34(9):906-911, September 2007.

What is claimed:

1. A method for treating a subject having an inflammatory disease or medical condition comprising administering to the subject dicyanocobinamide that binds nitric oxide synthase (NOS) but not nitric oxide (NO) so as to inhibit nitric oxide synthase (NOS) but not nitric oxide,
wherein the inflammatory disease or medical condition is selected from a group consisting of inflammation, inflammatory bowel disease, nephritis, glomerulonephritis, hepatitis, arteritis, vasculitis, cerebritis, dermatitis, hypotension, arthritis, sepsis, septic or cardiogenic shock and myocardial infarction,
thereby treating the subject having the inflammatory or neurological disease or medical condition.

2. The method of claim 1, wherein said dicyanocobinamide is administered in an amount about 0.1 mg/kg to 100 mg/kg weight of a subject, about 0.5 to 5 mg/kg weight of a subject, about 5 to 10 mg/kg weight of a subject, about 10 to 15 mg/kg weight of a subject, about 15 to 20 mg/kg weight of a subject, about 20 to 25 mg/kg weight of a subject, about 25 to 30 mg/kg weight of a subject, about 30 to 35 mg/kg weight of a subject, about 35 to 40 mg/kg weight of a subject, about 40 to 45 mg/kg weight of a subject, about 45 to 50 mg/kg weight of a subject, about 50 to 55 mg/kg weight of a subject, about 55 to 60 mg/kg weight of a subject, about 60 to 65 mg/kg weight of a subject, about 65 to 70 mg/kg weight of a subject, about 70 to 75 mg/kg weight of a subject, about 75 to 80 mg/kg weight of a subject, about 80 to 85 mg/kg weight of a subject, about 85 to 90 mg/kg weight of a subject, about 90 to 95 mg/kg weight of a subject, about 95 to 100 mg/kg weight of a subject, about 2 to 10 mg/kg weight of a subject, about 0.1 to 4 mg/kg weight of a subject, about 0.1 to 0.5 mg/kg weight of a subject, about 0.5 to 1.0 mg/kg weight of a subject, about 1.0 to 1.5 mg/kg weight of a subject, about 1.5 to 2.0 mg/kg weight of a subject, about 2.0 to 2.5 mg/kg weight of a subject, about 2.5 to 3.0 mg/kg weight of a subject, about 3.0 to 3.5 mg/kg weight of a subject, about 3.5 to 4.0 mg/kg weight of a subject, about 4.0 to 4.5 mg/kg weight of a subject, about 4.5 to 5.0 mg/kg weight of a subject, about 5.0 to 5.5 mg/kg weight of a subject, about 5.5 to 6.0 mg/kg weight of a subject, about 6.0 to 6.5 mg/kg weight of a subject, about 6.5 to 7.0 mg/kg weight of a subject, about 7.0 to 7.5 mg/kg weight of a subject, about 7.5 to 8.0 mg/kg weight of a subject, about 8.0 to 8.5 mg/kg weight of a subject, about 8.5 to 9.0 mg/kg weight of a subject, about 9.0 to 9.5 mg/kg weight of a subject, about 9.5 to 10.0 mg/kg weight of a subject, about 0.1 to 2 mg/kg weight of a subject, about 2 to 4 mg/kg weight of a subject, about 4 to 6 mg/kg weight of a subject, about 6 to 8 mg/kg weight of a subject, about 8 to 10 mg/kg weight of a subject, about 10 to 12 mg/kg weight of a subject, about 12 to 14 mg/kg weight of a subject, about 14 to 16 mg/kg weight of a subject, about 16 to 18 mg/kg weight of a subject, about 18 to 20 mg/kg weight of a subject, about 0.5 mg/kg weight of a subject, 2 mg/kg weight of a subject, 10 mg/kg weight of a subject, about 0.5 mg/kg to 100 mg/kg weight of a subject, about 0.5 to 10 mg/kg weight of a subject, about 0.1 mg/kg to 20 mg/kg weight of a subject, about 500 mg for a subject weighing less than 60 kg, 750 mg for a subject weighing between 60-100 kg, 1000 mg for a subject weighing more than 100 kg, about 0.1 gram per dose, about 0.5 gram per dose, about 1 gram per dose, about 2 gram per dose, about 3 gram per dose, about 4 grain per dose, about 5 gram per dose, about 6 gram per dose, about 7 gram per dose, about 8 gram per dose, about 9 gram per dose, about 10 gram per dose, about 11 gram per dose, about 12 gram per dose, about 13 gram per dose, about 14 gram per dose, about 15 gram per dose, about 16 gram per dose, about 17 gram per dose, about 18 gram per dose, about 19 gram per dose or about 20 gram per dose.

3. The method of claim 1, wherein said dicyanocobinamide is administered orally, intravenously, intrarectally, intravaginally, intrabronchially, topically, intramuscularly, intraperitoneally, intrapleurally, by inhalation, by eye drops or by any enteral, parenteral or non-parenteral mechanism.

* * * * *